(12) United States Patent
Asano et al.

(10) Patent No.: US 8,702,963 B2
(45) Date of Patent: Apr. 22, 2014

(54) ELECTROCHEMICAL MEASUREMENT ELECTRODE, ELECTROCHEMICAL MEASUREMENT ELECTRODE CHIP, AND ELECTROCHEMICAL MEASURING METHOD AND ANALYSIS METHOD USING THE SAME

(75) Inventors: Naomi Asano, Osaka (JP); Yuichiro Shimizu, Osaka (JP); Yoshiro Akagi, Osaka (JP); Ikuo Nakano, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 333 days.

(21) Appl. No.: 12/930,994

(22) Filed: Jan. 19, 2011

(65) Prior Publication Data

US 2011/0174636 A1 Jul. 21, 2011

(30) Foreign Application Priority Data

Jan. 20, 2010 (JP) .................................. 2010-10422

(51) Int. Cl.
*G01N 27/26* (2006.01)

(52) U.S. Cl.
USPC ........ 205/789; 204/435; 204/416; 435/287.1; 422/68.1; 422/82.01

(58) Field of Classification Search
USPC ............... 204/403.01–403.15, 435, 416, 434; 205/789; 435/287.1; 422/68.1, 82.01
See application file for complete search history.

(56) References Cited

U.S. PATENT DOCUMENTS

| | | | |
|---|---|---|---|
| 5,034,113 A | 7/1991 | Iwamoto | |
| 2003/0209435 A1 | 11/2003 | Iwamoto et al. | |
| 2004/0014023 A1* | 1/2004 | Meserol et al. | 435/2 |
| 2008/0011607 A1 | 1/2008 | Iwamoto et al. | |
| 2011/0079523 A1* | 4/2011 | Offenbacher et al. | 205/793 |

FOREIGN PATENT DOCUMENTS

| | | |
|---|---|---|
| JP | 61-209351 A | 9/1986 |
| JP | 61-270652 A | 11/1986 |
| JP | 2-107959 A | 4/1990 |
| JP | 3760137 B2 | 3/2006 |
| JP | 2007-232563 A | 9/2007 |
| JP | 2007-278981 A | 10/2007 |
| WO | WO 2009/090094 * | 7/2009 |

OTHER PUBLICATIONS

Li et al. (Analytica Chimica Acta. 229, 1990, 213-219).*
Ito et al. (Talanta, 42, 1995, 1685-1690).*

* cited by examiner

*Primary Examiner* — Jennifer Dieterle
(74) *Attorney, Agent, or Firm* — Edwards Wildman Palmer LLP; David G. Conlin; David A. Tucker

(57) ABSTRACT

In order to realize an accurate electrochemical measurement without a peak caused due to a silver chloride complex ion, an electrochemical measurement electrode of the present invention which measures an electrochemical active substance in a sample solution containing a chloride ion includes (i) a working electrode, (ii) a reference electrode made of silver and silver chloride, and (iii) a silver ion capturing material which captures a silver ion out of a silver chloride complex ion generated in the reference electrode.

19 Claims, 22 Drawing Sheets

(a) FRONT (b) REAR (c) BOTTOM (a) FRONT (b) REAR (c) BOTTOM (a) FRONT (b) REAR (c) BOTTOM (a) FRONT (b) REAR (c) BOTTOM (a) FRONT (b) REAR (c) BOTTOM (a) FRONT (b) REAR (c) BOTTOM (a)

(b)

US 8,702,963 B2

ELECTROCHEMICAL MEASUREMENT ELECTRODE, ELECTROCHEMICAL MEASUREMENT ELECTRODE CHIP, AND ELECTROCHEMICAL MEASURING METHOD AND ANALYSIS METHOD USING THE SAME

This Nonprovisional application claims priority under 35 U.S.C. §119(a) on Patent Application No. 2010-010422 filed in Japan on Jan. 20, 2010, the entire contents of which are hereby incorporated by reference.

TECHNICAL FIELD

The present invention relates to an electrochemical measurement electrode, an electrochemical measurement electrode chip, and an electrochemical measuring method and an analysis method using the electrochemical measurement electrode and the electrochemical measurement electrode chip.

BACKGROUND ART

An electrochemical measuring method which makes use of an electrochemical reaction in a solution has been often used in analyses in fields such as a biological field, an environmental field, a medical field, and a food field. For example, an immunoanalytical method utilizing an electrochemical detection is used for analyzing trace substances (such as protein and hormone) in a biologic sample. An electrochemical measurement electrode used in such an analysis is configured by providing, on a substrate, predetermined electrodes (such as a working electrode and a reference electrode) made of a conductive material. For example, Patent Literature 1 discloses a flat electrochemical measurement electrode in which a working electrode, a counter electrode, and a reference electrode are provided on an insulating substrate by patterning a conductive material.

Patent Literature 2 discloses an electrochemical measurement electrode in which an electrode made of a noble metal is provided on part of a printed section on a printed-wiring board and the rest of the printed section is insulated by an insulator.

According to the electrochemical measurement electrodes disclosed in Patent Literatures 1 and 2, an electrode made of silver and silver chloride is used as the reference electrode. Such an electrode made of silver and silver chloride is one of reference electrodes which have been widely used, because the electrode (i) has a simple structure and thereby is easy to handle and (ii) has good reproducibility of an electric potential.

Patent Literature 3 discloses a comparison electrode which includes an internal liquid in which an inner electrode made of silver and silver chloride is disposed. Such a comparison electrode is used in a pH measurement, etc. Specifically, a pH measurement of a target solution is carried out with the use of (i) the comparison electrode in which the internal liquid is sealed and (ii) another electrode which is disposed in the target solution and is separated from the internal liquid. According to the technique disclosed in Patent Literature 3, an inorganic cation-exchange agent, which captures a silver ion and/or a chloro complex ion, is provided in the comparison electrode for preventing deposition of the silver chloride in the internal liquid.

CITATION LIST

Patent Literature

Patent Literature 1
  Japanese Patent Application Publication, Tokukai, No. 2007-278981 (Publication Date: Oct. 25, 2007)
Patent Literature 2
  Japanese Patent Application Publication, Tokukaisyo, No. 61-270652 (Publication Date: Nov. 29, 1986)
Patent Literature 3
  Japanese Patent No. 3760137 (Registration Date: Jan. 13, 2006)

SUMMARY OF INVENTION

Technical Problem

However, there is a problem that an abnormal peak is detected in a case where an CV (cyclic voltammetry) measurement is carried out with the use of an electrochemical measurement electrode including (i) a reference electrode made of sliver and silver chloride, (ii) a working electrode, and (iii) a counter electrode.

For example, in a case where a CV measurement is carried out on a sample solution having a chloride ion concentration of 150 mM, an abnormal peak occurred due to an AgCl complex ion appears on an obtained CV curve. The abnormal peak appears around ±50 mV to 60 mV (vs. Ag/AgCl) in a case where the abnormal peak is small. As the peak becomes large, the abnormal peak appears around ±70 mV to 90 mV. In the example of a CV curve shown in FIG. 35, peaks appearing around ±0.1 V are the abnormal peaks caused due to the AgCl complex ion. This phenomenon occurs more notably as the chloride ion concentration of the sample solution is increased. On the other hand, the chloride ion in the sample solution is necessary for achieving reproducibility of an electric potential. In a case where a minute electric current of nanoampere to submicroampere order is measured, it is impossible, due to the abnormal peaks, to accurately obtain a detected value regarding a substance to be measured in the sample solution. Moreover, it is impossible to carry out an accurate measurement not only in the CV measurement, but also in a chronoamperometry measurement and a chronocoulometry measurement, because an obtained measurement value is a detected value affected by the abnormal peak.

According to the electrochemical measurement electrodes disclosed in Patent Literatures 1 and 2, an electrode made of silver and silver chloride is used as the reference electrode. However, no measure is provided for capturing AgCl complex ion which (i) is generated from the electrode made of silver and silver chloride and (ii) causes an abnormal peak.

Moreover, according to the technique disclosed in Patent Literature 3, no electrode is provided so as to be paired with the comparison electrode including, in an internal liquid, an inner electrode made of silver and silver chloride. That is, the technique disclosed in Patent Literature 3 is not a technique regarding an electrochemical measurement electrode. The above mentioned problem as to the abnormal peak caused due to the AgCl complex ion occurs in the electrochemical measurement electrode which includes the reference electrode made of silver and silver chloride, the working electrode, and the counter electrode. That is, the problem of the abnormal peak occurs when the AgCl complex ion dissolved in the solution to be measured reaches the working electrode, and electrons are exchanged. In other words, the problem of the abnormal peak occurs in an electrochemical measurement electrode used for measuring the exchange of electrons between the reference electrode made of silver and silver chloride and the working electrode which are present in the solution to be measured. According to the configuration disclosed in Patent Literature 3, the AgCl complex ion dissolved out of the inner electrode made of silver and silver chloride does not reach another electrode. This configuration is fundamentally different from that of an electrochemical measurement electrode. Therefore, the technique disclosed in Patent Literature 3 does not involve the problem of the abnormal peak caused due to the AgCl complex ion.

Solution to Problem

The present invention is accomplished in view of the problems, and its object is to provide (i) an electrochemical measurement electrode and an electrochemical measurement electrode chip with which an accurate detection can be carried out, and (ii) an electrochemical measuring method and an analysis method using the electrochemical measurement electrode and the electrochemical measurement electrode chip.

In order to attain the object, the inventors conducted detailed study regarding the abnormal peak. As a result, it has turned out that the abnormal peak is caused due to a silver chloride complex ion ($[AgCL_2]^-$, $[AgCL_3]^{2-}$, and $[AgCL_4]^{3-}$) generated from the reference electrode made of silver and silver chloride. The silver chloride constituting the reference electrode progressively reacts as indicated by the formulae below under the presence of a chloride ion in the solution. In the formulae below, the symbol "↔" indicates directions of a forward reaction and an inverse reaction. The chemical reaction formulae connected via the symbol "↔" indicate a so-called equilibration reaction.

$$AgCl + Cl^- + Cl^- \leftrightarrow [AgCl_2]^-$$

$$[AgCl_2]^- + Cl^- \leftrightarrow [AgCl_3]^{2-}$$

$$[AgCl_3]^{2-} + Cl^- \leftrightarrow [AgCl_4]^{3-}$$

In this way, a silver chloride complex ion is generated and dissolved in the sample solution. The silver chloride complex ion causes electrochemical reaction at the working electrode, and thereby the electrochemical reaction is detected as the abnormal peak. From this, the inventor has found that the problems can be solved by eliminating the silver chloride complex ion.

Further, the inventor has found that a concentration of the silver chloride complex ion can be reduced by eliminating a silver ion from a measurement system as indicated by a formula below, and the above described object can be attained by providing a silver ion capturing material in the electrochemical measurement electrode. In this way, the present invention is accomplished.

$$[AgCl_2]^- \leftrightarrow Ag^+ + 2CL^-$$

In order to attain the object, an electrochemical measurement electrode of the present invention (i) is used in measuring an electrochemical active substance in a sample solution containing a chloride ion and (ii) includes: a working electrode; a reference electrode made of silver and silver chloride; and a silver ion capturing material which captures a silver ion out of a silver chloride complex ion generated from the reference electrode. Moreover, it is preferable that the working electrode, the reference electrode, and the silver ion capturing material are provided so as to contact with the sample solution.

The term "silver ion capturing material" indicates a substance which captures a silver ion out of a silver chloride complex ion generated in a reaction of (i) a silver chloride contained in the reference electrode and (ii) a chloride ion in the sample solution, so as to eliminate the silver chloride complex ion which causes an abnormal detection (abnormal peak). To "capture a silver ion" indicates to incorporate a silver ion into the silver ion capturing material itself or to adsorb a silver ion on a surface of the silver ion capturing material. In a case where the silver ion is incorporated in the silver ion capturing material, the silver ion is directly incorporated or the silver ion which has been changed into another substance is incorporated.

According to the configuration, the silver chloride complex ion generated from the reference electrode is changed into a chloride ion by the silver ion capturing material and thereby the silver chloride complex ion can be eliminated. Therefore, according to the configuration, a desired electrochemical measurement can be carried out without detecting an abnormal peak caused due to a silver chloride complex ion. This makes it possible to provide the electrochemical measurement electrode with which accurate detection and measurement can be carried out.

In order to attain the object, an electrochemical measurement electrode chip of the present invention includes: the above described electrochemical measurement electrode; and a microchip which covers the electrochemical measurement electrode, the microchip having (i) a hollowed section which contains therein the working electrode and the reference electrode and (ii) an inlet section via which the sample solution is fed into a measurement section which is an area defined by the electrochemical measurement electrode and the hollowed section.

According to the configuration, a reduction of an amount of the sample solution, a reduction of measurement time, and a simplification of an analysis operation can be achieved. This makes it possible to realize an accurate and efficient measurement.

In order to attain the object, an electrochemical measuring method of the present invention uses the above described electrochemical measurement electrode and includes the steps of: dipping the electrochemical measurement electrode in the sample solution containing the chloride ion and the electrochemical active substance, the electrochemical measurement electrode being dipped so that, at least partially, each of the working electrode, the reference electrode, and the silver ion capturing material contacts with the sample solution; and measuring the electrochemical active substance in the sample solution.

According to the configuration, in the dipping step, the electrochemical measurement electrode is dipped in the sample solution containing the chloride ion and the electrochemical active substance so that, at least partially, each of the working electrode, the reference electrode, and the silver ion capturing material contacts with the sample solution. This allows the silver ion capturing material to eliminate the silver chloride complex ion out of the sample solution. Accordingly, an accurate electrochemical measurement can be carried out.

In order to attain the object, an electrochemical measuring method of the present invention uses the above described electrochemical measurement electrode chip and includes the steps of: feeding the sample solution containing the chloride ion and the electrochemical active substance into the measurement section via the inlet section; and measuring the electrochemical active substance in the sample solution.

According to the configuration, in the feeding step, the sample solution containing the chloride ion and the electrochemical active substance is fed into the measurement section via the inlet section. This allows the silver ion capturing material to eliminate the silver chloride complex ion out of the sample solution. Accordingly, an accurate electrochemical measurement can be carried out. Further, the electrochemical measurement can be carried out in short time with a small amount of the solution.

In order to attain the object, an analysis method of the present invention (i) uses an electrochemical measurement electrode including a working electrode on which a reactive substance which specifically reacts with a detection substance is at least partially fixed and (ii) includes the steps of: dipping the electrochemical measurement electrode in the sample solution containing the detection substance, the electrochemical measurement electrode being dipped so that, at least partially, each of the working electrode, the reference electrode, and the silver ion capturing material contacts with the sample solution; and measuring, under the presence of the chloride ion, the electrochemical active substance generated in a reaction of the reactive substance and the detection substance.

According to the configuration, in the dipping step, the electrochemical measurement electrode is dipped in the sample solution containing the detection substance so that, at least partially, each of the working electrode, the reference electrode, and the silver ion capturing material contacts with the sample solution. This allows the reactive substance fixed on the working electrode to react with the detection substance. Then, in the measuring step, the electrochemical active substance generated by the reaction is measured under the presence of the chloride ion. In this case, the silver chloride complex ion being in the measurement system can be eliminated by the silver ion capturing material, and thereby an accurate analysis can be carried out.

In order to attain the object, an analysis method of the present invention (i) uses an electrochemical measurement electrode chip including a working electrode on which a reactive substance which specifically reacts with a detection substance is at least partially fixed and (ii) includes the steps of: feeding the sample solution containing the detection substance into the measurement section via the inlet section; and measuring, under the presence of the chloride ion, the electrochemical active substance generated in a reaction of the reactive substance and the detection substance.

According to the configuration, in the feeding step, the sample solution containing the detection substance is fed into the measurement section via the inlet section. This allows the reactive substance fixed on the working electrode to react with the detection substance. Then, in the measuring step, the electrochemical active substance generated by the reaction is measured under the presence of the chloride ion. In this case, the silver chloride complex ion being in the measurement system can be eliminated by the silver ion capturing material, and thereby an accurate analysis can be carried out in short time with a small amount of the sample solution.

Advantageous Effects Of Invention

According to the present invention, it is possible to carry out accurate electrochemical measurement and analysis without an abnormal peak caused due to the silver chloride complex ion.

DESCRIPTION OF EMBODIMENTS

The present invention relates to (i) an electrochemical measurement electrode suitable for use in analyses in fields such as a biological field, an environmental field, a medical field, and a food field and (ii) an electrochemical detection sensor including the electrochemical measurement electrode.

The following describes details of a best mode of the present invention, with reference to FIGS. 1 through 32.

[Embodiment 1]
[Embodiment 1-1]
[Embodiment 1-1-1]

Figure 1:
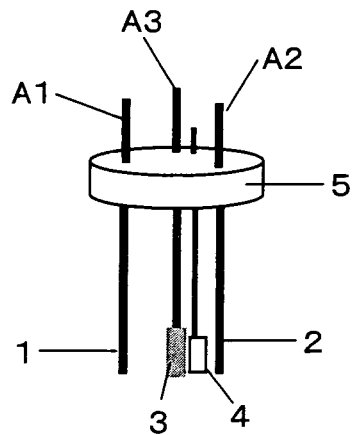
FIG. 1 is a perspective view schematically illustrating a structure of an electrochemical measurement electrode of Embodiment 1-1-1.

FIG. 1 is a perspective view schematically illustrating a structure of an electrochemical measurement electrode of Embodiment 1-1-1.

The electrochemical measurement electrode shown in FIG. 1 includes a working electrode 1, a counter electrode 2, a reference electrode 3 made of silver and silver chloride, a silver ion capturing material 4, and an electrode holder 5. The working electrode 1, the counter electrode 2, and the reference electrode 3 are provided so as to pierce the electrode holder 5 which has a columnar shape. Further, the silver ion capturing material 4 is provided on the electrode holder 5, as with the working electrode 1, the counter electrode 2, and the reference electrode 3.

The electrode holder 5 is a base on which the working electrode 1, the counter electrode 2, the reference electrode 3, and the silver ion capturing material 4 are provided. According to the present embodiment, the electrode holder 5 has a columnar shape. However, the shape of the electrode holder 5 is not limited to a particular one, that is, the shape does not necessarily need to be the columnar shape. The electrode holder 5 can be made of, for example, an insulation material such as glass, quartz, ceramics, or plastic.

The working electrode 1 is an electrode which is used for detecting, by an electrochemical reaction (oxidation or reduction), an electrochemical active substance contained in a sample solution. According to the electrochemical measurement electrode shown in FIG. 1, the working electrode 1 has a long and thin bar-like shape. However, the shape of the working electrode 1 is not limited to a particular one, that is, the shape does not necessarily need to be the shape shown in FIG. 1. For example, the working electrode 1 can be disposed on an apical end of a bar while having a rectangular shape, a round shape, an elliptical shape, a half round shape, or any other shape. Moreover, a size of the working electrode 1 is not limited in particular, and can be appropriately set in accordance with a size of the electrochemical measurement electrode. The working electrode 1 can be made of, for example, a conductive material such as metal, carbon, or graphite.

The counter electrode 2 is an electrode through which a current generated in the working electrode 1 flows. According to the electrochemical measurement electrode of the present embodiment, the counter electrode 2 can be replaced with the reference electrode 3, and accordingly does not necessarily need to be provided. However, in order to carry out a more accurate electrochemical measurement, it is preferable to provide the counter electrode 2. According to the electrochemical measurement electrode shown in FIG. 1, the counter electrode 2 has a long and thin bar-like shape, as with the working electrode 1. However, the shape of the counter electrode 2 is not limited to a particular one, that is, the shape does not necessarily need to be the shape shown in FIG. 1. For example, the counter electrode 2 can be disposed on an apical end of a bar while having a rectangular shape, a round shape, an elliptical shape, a half round shape, or any other shape.

The counter electrode 2 is not limited in particular in terms of its size. However, it is preferable that the counter electrode 2 has a size which is at the same level as that of the working electrode 1 or has a size larger than that of the working electrode 1. This is because, in a case where the counter electrode 2 is far smaller than the working electrode 1, a current becomes difficult to flow and thereby an accurate electrochemical measurement cannot be carried out, since the counter electrode 2 is an electrode through which the current generated in the working electrode 1 flows, as described above. The counter electrode 2 can be made of a material which is similar to that of the working electrode 1.

The reference electrode 3 is an electrode used for applying a desired stable electric potential to the working electrode 1. It is preferable that the reference electrode 3 is provided as close as possible to the working electrode 1, in consideration of occurrence of an IR drop due to a solution resistance. According to the electrochemical measurement electrode shown in FIG. 1, the reference electrode 3 has a long and thin bar-like shape. However, the shape of the reference electrode 3 is not limited to a particular one, that is, the shape does not necessarily need to be the shape shown in FIG. 1. For example, the reference electrode 3 can be disposed on an apical end of a bar while having a rectangular shape, a round shape, an elliptical shape, a half round shape, or any other shape. The reference electrode 3 is not limited in particular in terms of its size, but it is preferable that the size is small.

The reference electrode 3 is made of silver and silver chloride. Such a reference electrode 3 can be formed with the use of a conventionally known method. Such a method for forming the reference electrode 3 can be, for example, (i) a method in which an electrode made of silver is formed first and then part of the electrode thus formed is electrically or chemically changed into silver chloride or (ii) a method in which the reference electrode 3 is formed with the use of ink in which silver and silver chloride are mixed together at an arbitrary ratio.

Moreover, according to the electrochemical measurement electrode of the present embodiment, connection pads A1 through A3 are provided above the electrode holder 5. The connection pads A1 through A3 are used for connecting the electrochemical measurement electrode with an electrochemical measuring device (such as a potentiostat). The respective connection pads A1 through A3 are provided for connecting the electrochemical measuring device with the working electrode 1, the counter electrode 2, and the reference electrode 3. Positions of the respective connection pads A1 through A3 can be set as appropriate in accordance with connection positions with the electrochemical measuring device, and are not limited in particular as long as the respective connection pads A1 through A3 can connect the working electrode 1, the counter electrode 2, and the reference electrode 3 with the electrochemical measuring device. According to the electrochemical measurement electrode shown in FIG. 1, each of the connection pads A1 through A3 has a bar-like shape. However, the shape of each of the connection pads A1 through A3 is not limited to a particular one, that is, the shape does not necessarily needs to be the shape shown in FIG. 1. Moreover, each of the connection pads A1 through A3 only needs to have a size with which the connection pads A1 through A3 can sufficiently contact with connection pads provided on the electrochemical measuring device. Moreover, each of the connection pads A1 through A3 only needs to be made of a conductive material. Each of the connection pads A1 through A3 can be made of a material which is similar to that of the working electrode 1, the counter electrode 2, and the reference electrode 3. Alternatively, each of the connection pads A1 through A3 can be made of a material which is different from that of the working electrode 1, the counter electrode 2, and the reference electrode 3.

The silver ion capturing material 4 is a member which captures a silver ion out of the silver chloride complex ion generated from the reference electrode 3. The silver ion capturing material 4 captures the silver ion, and consequently, the silver chloride complex ion in the sample solution is eliminated.

The silver ion capturing material 4 is disposed in a part which is to contact with the sample solution which is an object of an electrochemical measurement. The silver chloride complex ion is generated from the reference electrode 3 under the presence of the chloride ion in the sample solution. Therefore, it is preferable that the silver ion capturing material 4 is disposed closer to the reference electrode 3 than to the working electrode 1. It is further preferable that the silver ion capturing material 4 is provided in an area corresponding to a layer which is formed around the reference electrode 3 and has a concentration gradient of the silver chloride complex ion.

According to the electrochemical measurement electrode shown in FIG. 1, the silver ion capturing material 4 having a rectangular shape is provided on a bar-like shaped base. However, the shape of the silver ion capturing material 4 is not limited to a particular one, that is, the shape does not necessarily need to be the shape show in FIG. 1. For example, the silver ion capturing material 4 can have a rectangular shape, a round shape, an elliptical shape, a half round shape, or any other shape. The silver ion capturing material 4 is not limited in particular in terms of its size, but it is preferable that the silver ion capturing material 4 has a length of approximately 1 mm or longer.

The silver ion capturing material 4 can be made of, for example, a cation-exchange agent. More specifically, the silver ion capturing material 4 can be made of a cation-exchange agent such as a cation-exchange resin or zeolite. Each of these cation-exchange agents has a function to (i) capture a silver ion out of a silver chloride complex ion, (ii) exchange the silver ion for another cation (such as a sodium ion or a potassium ion), and (iii) discharge the another cation into the sample solution. Therefore, with the use of any of these cation-exchange agents, the silver chloride complex ion generated from the reference electrode 3 can be eliminated.

The silver ion capturing material 4 can be formed by an arbitrary method in which a cation-exchange agent as the silver ion capturing material 4 is fixed on a part of the base which part is to contact with the sample solution. For example, the silver ion capturing material 4 can be formed by (i) a method in which a cation-exchange agent is fixed by an adhesive agent or (ii) a method in which a cation-exchange agent is mixed with a thermosetting resin or a light-curing resin, and then the mixture is fixed by hardening the resin by heating or irradiating the resin with light.

According to Embodiment 1-1-1, the silver ion capturing material can be made of a material which encompasses a cured resin which is a light-curing resin or a thermosetting resin which is mixed with a silver ion exchange agent. The "cured resin" in this specification encompasses a gel material, as well as a completely hardened material such as plastic.

[Embodiment 1-1-2]

The following describes a modified configuration of Embodiment 1-1-1, with regard to the configuration of the electrochemical measurement electrode of Embodiment 1-1. An electrochemical measurement electrode of the present Embodiment 1-1-2 is similar to that of Embodiment 1-1-1, except that the silver ion capturing material 4 is made of a cation adsorbent. Since the electrochemical measurement electrode of Embodiment 1-1-2 has a configuration similar to that of shown in FIG. 1, an explanation for the configuration is omitted here.

The term "cation adsorbent" indicates a material which takes in a cation by a chemical binding (hydrogen binding, ion binding, coordinate binding). Such a "cation adsorbent" can be made of, for example, a chelate resin, ceramics, or mesoporous silica. The chelate resin is a resin having a functional group which chelate-bonds with a particular metal ion. It is preferable that the chelate resin has a property not to adsorb an alkali metal ion or an alkaline-earth metal but to selectively adsorb a transition metal ion such as a silver ion.

The ceramics can be used as a material having adsorptive capacity to a cation. Such ceramics can be, for example, porous ceramics which has pores for adsorbing cations. In a case where porous ceramics is used, it is possible to prepare porous ceramics which adsorbs only a silver ion by adjusting a size of pores and a state of a surface of the porous ceramics. The use of such porous ceramics is further effective.

The mesoporous silica can be used as a material having adsorptive capacity to a cation, as with the ceramics. Further, it is possible to prepare mesoporous silica which adsorbs only a silver ion by adjusting a size of pores and a state of surface of the mesoporous silica. The use of such mesoporous silica is further effective.

The cation adsorbent can take in a silver ion in the silver chloride complex ion by a chemical binding (hydrogen binding, ion binding, coordinate binding). Therefore, with the use of the cation adsorbent, it is possible to eliminate the silver chloride complex ion generated from the reference electrode 3.

The silver ion capturing material 4 can be formed by any method as long as the cation adsorbent as the silver ion capturing material 4 is fixed on a part of the base which part is to contact with the sample solution. It is possible to use the method for forming the silver ion capturing material 4 described in Embodiment 1-1-1 for example.

Accordingly, a constituent material of the silver ion capturing material of Embodiment 1-1-2 encompasses a cured resin which is a light-curing resin or a thermosetting resin mixed with a silver ion adsorbent.

[Embodiment 1-1-3]

The following describes another modification of the configuration of Embodiment 1-1-1, with regard to the configuration of the electrochemical measurement electrode of Embodiment 1-1. An electrochemical measurement electrode of the present Embodiment 1-1-3 is similar to that of Embodiment 1-1-1, except that the silver ion capturing material 4 is made of a silver ion reducing agent. Since the electrochemical measurement electrode of Embodiment 1-1-3 has a configuration similar to that of shown in FIG. 1, an explanation for the configuration is omitted here.

The term "silver ion reducing agent" indicate a material having a property of reducing a silver ion to silver. The silver ion reducing agent reduces the silver ion in the silver chloride complex ion to silver, and thereby the silver chloride complex ion generated from the reference electrode 3 is eliminated.

The silver ion reducing agent is not limited in particular as long as the silver ion reducing agent is a material having a reductive capacity to reduce a silver ion to silver. For example, the silver ion reducing agent can be (i) a compound having an aldehyde (CHO) group or (ii) a metal which has a ionization tendency higher than that of silver.

The aldehyde group is a functional group having a reducing property. Therefore, the silver ion in the silver chloride complex ion is reduced to silver due to the function of a compound having the aldehyde group, and thereby the silver chloride complex ion generated from the reference electrode 3 is eliminated. The compound having the aldehyde group can be, for example, aldehyde or formic acid.

In a case where a solution, which contains two types of metal elements having respectively different ionization tendencies, is used, a metal element having a higher ionization tendency is ionized and becomes prone to emit an electron. On the other hand, a metal element having a lower ionization tendency receives the emitted electron and is thereby deposited as solid metal. With the use of this principle, the silver chloride complex ion can be eliminated. That is, in a case where the silver ion capturing material 4 is made of a metal element having an ionization tendency lower than that of silver, the silver ion in the silver chloride complex ion receives an electron emitted in ionization of the metal element, and thereby the silver ion is deposited as silver. This makes it possible to eliminate the silver chloride complex ion generated from the reference electrode 3. In a case where a metal element is used as the silver ion reducing agent, the metal element is not limited in particular as long as the metal element has an ionization tendency higher than that of silver. However, it is preferable that the metal element is magnesium (Mg), aluminum (Al), manganese (Mn), zinc (Zn), chromium (Cr), iron (Fe), cadmium (Cd), cobalt (Co), tin (Sn), lead (Pb), or copper (Cu), because these elements can be used in a water system. In particular, among the above described metal elements, magnesium (Mg), aluminum (Al), zinc (Zn), or copper (Cu) is preferable in terms of toxicity and handiness.

In a case where the silver ion reducing agent is a solid, the silver ion capturing material 4 can be prepared with a method similar to those described in Embodiment 1-1-1 and Embodiment 1-1-2. In a case where the cation reducing agent is a liquid (a compound having an aldehyde group), the silver ion capturing material 4 can be prepared with a method in which the cation reducing agent is reacted with a light-curing resin or a thermosetting resin so as to prepare a resin in which an aldehyde group as a functional group is introduced to a side chain of the resin, and then thus prepared resin is hardened. This method can be applied to a case where the cation reducing agent is a solid.

In a case where the silver ion reducing agent is a metal having an ionization tendency higher than that of silver in particular, a method such as a sputtering method, an evaporation method, or a printing method can be used, other than the above described method. Further, it is possible to use a method such as (i) a method of fixing a solid metal by an adhesive agent or (ii) a method in which a mixture of powdered solid metal and a light-curing resin or a thermosetting resin is prepared, and then the mixture is hardened by irradiating the mixture with light or heating the mixture.

Accordingly, a constituent material of the silver ion capturing material of Embodiment 1-1-3 encompasses (i) a cured resin which is a light-curing resin or a thermosetting resin mixed with a silver ion reducing agent or (ii) a cured resin in which an aldehyde group as a functional group is introduced to a side chain of a light-curing resin or a thermosetting resin.

(Arrangement of Silver Ion Capturing Material 4)

Figure 2:
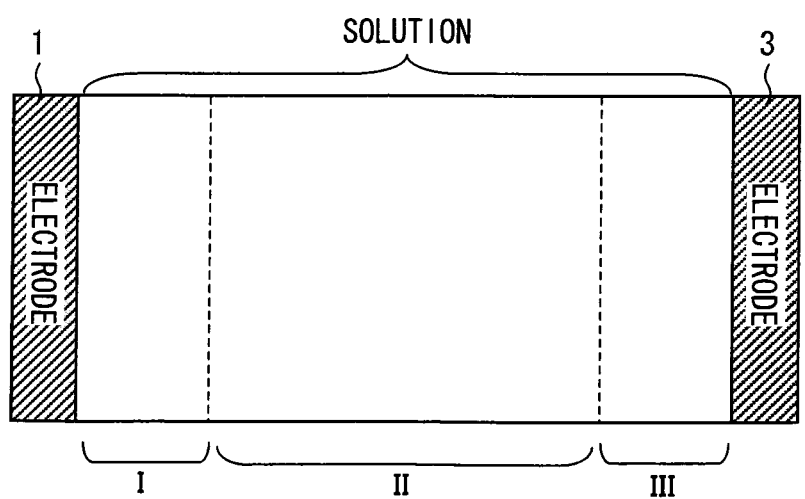
FIG. 2 is a schematic view illustrating a sample liquid (solution) existing between a working electrode and a reference electrode.

The following describes details of an arrangement of the silver ion capturing material 4 in the electrochemical measurement electrode of the present embodiment. It is preferable that the silver ion capturing material 4 is disposed in an area corresponding to a diffusion layer which is formed around the working electrode 1. The term "diffusion layer" indicates a thin layer (i) which contacts with an electrode in the sample solution and (ii) in which a concentration gradient is generated in contrast to the bulk of the sample solution due to mass transfer by diffusion. FIG. 2 is a schematic view illustrating the sample liquid (solution) existing between the working electrode 1 and the reference electrode 3.

As shown in FIG. 2, a diffusion layer I is formed in vicinity to the working electrode 1 in the solution, and a concentration gradient is generated in the diffusion layer I in contrast to the bulk of the solution due to mass transfer by diffusion. Moreover, a layer III is formed, in the solution, in vicinity to the reference electrode 3 from which the silver chloride complex ion is generated. In the layer III, a concentration gradient of the silver chloride complex ion is generated. The bulk of the solution which is between the diffusion layer I and the layer III is referred to as a solution bulk II.

A substance existing in the diffusion layer I can freely move, as in the solution bulk II. According to the electrochemical measurement electrode, a reacting species existing in the diffusion layer I can relate to an electrode reaction. A silver chloride complex ion which exists outside of the diffusion layer I (i.e., exists in the solution bulk II) does not relate to the reaction at the working electrode 1. However, in a case where a concentration of the silver chloride complex ion existing in the diffusion layer I is decreased due to the reaction at the working electrode 1, a silver chloride complex ion is newly supplied from the solution bulk II due to the concentration gradient.

The diffusion layer I is formed by only causing the working electrode 1 to contact with the solution, without applying an electric potential to the working electrode 1. When an electric potential is applied to the working electrode 1, a concentration distribution becomes larger due to ion transfer and an electrode reaction, and thereby the diffusion layer I expands. The diffusion layer I is, formed in an area within several tens of micrometers to 1 mm from the working electrode 1, depending on a concentration of the reacting species and an electric potential in the solution.

According to the electrochemical measurement electrode of the present embodiment, the silver chloride complex ion is generated from the reference electrode 3 and detected on the working electrode 1 as a peak. Therefore, in a case where the silver ion capturing material 4 is provided in vicinity to the working electrode 1 so as to eliminate the silver chloride complex ion, it is effective to eliminate a silver chloride complex ion existing in the diffusion layer I around the working electrode 1. That is, it is effective to prevent a silver chloride complex ion, which is supplied from the solution bulk II to the diffusion layer I, from approaching the working electrode 1. Such elimination of the silver chloride complex ion is effective, provided that the silver ion capturing material 4 is provided in an area corresponding to the diffusion layer I formed in vicinity to the working electrode 1, and the effect becomes higher as a distance from the silver ion capturing material 4 to the working electrode 1 becomes shorter.

On the other hand, the reference electrode 3 generates the silver chloride complex ion. Accordingly, a silver complex ion in the solution flows and spreads from the layer III to the solution bulk II due to the concentration gradient. Therefore, in a case where the silver ion capturing material 4 is provided in vicinity to the reference electrode 3 in order to eliminate the silver chloride complex ion as described in Embodiment 1-1, it is effective to prevent the silver chloride complex ion from flowing into the solution bulk II. Such elimination of the silver chloride complex ion is effective provided that the silver ion capturing material 4 is provided in, an area corresponding to the layer III which is to be formed in vicinity to the reference electrode 3, and the effect becomes higher as a distance from the silver ion capturing material 4 to the reference electrode 3 becomes shorter. Note that the layer III is to be formed in an area within approximately 1 mm from the reference electrode 3.

The following describes a configuration of Embodiment 1-2 in which the silver ion capturing material 4 is provided in vicinity to the working electrode 1 in order to eliminate a silver chloride complex ion.

[Embodiment 1-2]

Figure 3:
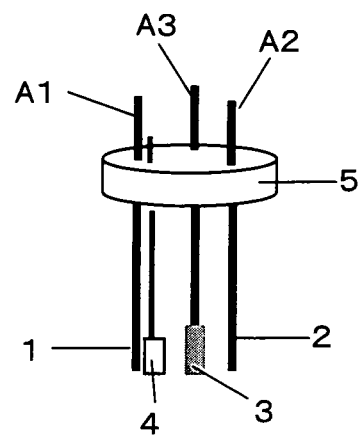
FIG. 3 is a perspective view schematically illustrating a structure of an electrochemical measurement electrode of Embodiment 1-2.

The following describes a modification of the configuration of Embodiment 1-1, with regard to the electrochemical measurement electrode of Embodiment 1. FIG. 3 is a perspective view schematically illustrating a structure of an electrochemical measurement electrode of the present Embodiment 1-2.

As shown in FIG. 3, according to the electrochemical measurement electrode of Embodiment 1-2, the silver ion capturing material 4 is provided in vicinity to the working electrode 1. In other words, the silver ion capturing material 4 is provided closer to the working electrode 1 than to the counter electrode 2 and the reference electrode 3.

According to the electrochemical measurement electrode of Embodiment 1-2, a silver chloride complex ion generated from the reference electrode 3 in the sample solution is to be eliminated by the silver ion capturing material 4 before reaching the working electrode 1 so as to cause an electrochemical reaction.

Moreover, according to the electrochemical measurement electrode of Embodiment 1-2, the silver ion capturing material can be made of a material which is similar to those described in Embodiments 1-1-1 through 1-1-3. That is, the silver ion capturing material 4 can be made of a cation-exchange agent (Embodiment 1-1-1), a cation adsorbent (Embodiment 1-1-2), or a silver ion reducing agent (Embodiment 1-1-3). With the use of these materials, it is possible to bring about an effect similar to those of Embodiments 1-1-1 through 1-1-3.

[Embodiment 1-3]

Figure 4:
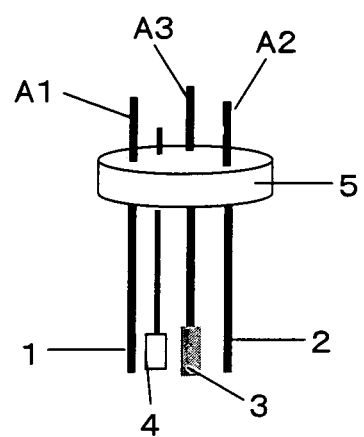
FIG. 4 is a perspective view schematically illustrating a structure of an electrochemical measurement electrode of Embodiment 1-3.

The following describes another modification of the configuration of Embodiment 1-1, with regard to the electrochemical measurement electrode of Embodiment 1. FIG. 4 is a perspective view schematically illustrating a structure of an electrochemical measurement electrode of the present Embodiment 1-3.

As shown in FIG. 4, according to the electrochemical measurement electrode of Embodiment 1-3, the silver ion capturing material 4 is provided between the working electrode 1 and the reference electrode 3.

According to the electrochemical measurement electrode of Embodiment 1-3, a silver chloride complex ion is eliminated by the silver ion capturing material 4 provided between the working electrode 1 and the reference electrode 3. This makes it possible to prevent the silver chloride complex ion, which is generated from the reference electrode 3 and emitted into the sample solution, from being diffused so as to reach the working electrode 1.

Moreover, according to the electrochemical measurement electrode of Embodiment 1-3, the silver ion capturing material 4 can be made of the material described in Embodiments 1-1-1 through 1-1-3. That is, the silver ion capturing material 4 can be made of a cation-exchange agent (Embodiment 1-1-1), a cation adsorbent (Embodiment 1-1-2), or a silver ion reducing agent (Embodiment 1-1-3). With the use of these materials, it is possible to bring about an effect similar to those of Embodiments 1-1-1 through 1-1-3.

[Embodiment 1-4]

Figure 5:
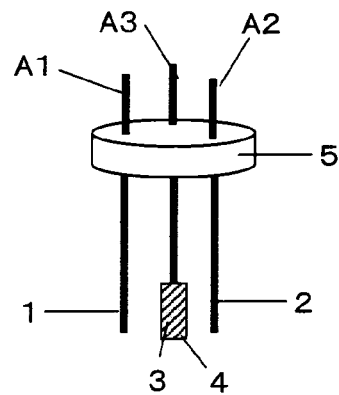
FIG. 5 is a perspective view schematically illustrating a structure of an electrochemical measurement electrode of Embodiment 1-4.

The following describes yet another modification of the configuration of Embodiment 1-1, with regard to the electrochemical measurement electrode of Embodiment 1. FIG. 5 is a perspective view schematically illustrating a structure of an electrochemical measurement electrode of the present Embodiment 1-4.

According to the electrochemical measurement electrode of Embodiment 1-4, the silver ion capturing material 4 is provided so as to cover the reference electrode 3 (see FIG. 5).

According to the electrochemical measurement electrode of Embodiment 1-4, the silver ion capturing material 4 covering the reference electrode 3 eliminates a silver chloride complex ion right after the silver chloride complex ion is generated from the reference electrode 3. Therefore, the silver chloride complex ion is not emitted into the sample solution (in the measuring system) and thereby the silver chloride complex ion can be eliminated more effectively.

The silver ion capturing material 4 can eliminate the silver chloride complex ion as long as the silver ion capturing material 4 is provided so as to cover at least part of a surface of the reference electrode 3. However, it is preferable that the silver ion capturing material 4 is provided so as to cover the whole surface of the reference electrode 3 (see FIG. 5). This makes it possible to eliminate almost all the silver chloride complex ions generated from the reference electrode 3.

Note that to "cover the whole surface of the reference electrode 3" does not mean completely sealing the whole surface of the reference electrode 3 with the silver ion capturing material 4 but means covering the reference electrode 3 so that the reference electrode 3 can supply an appropriate electric potential to the working electrode 1. According to the configuration in which the silver ion capturing material 4 covers the whole surface of the reference electrode 3, holes are formed in the silver ion capturing material 4 so that chloride ions can pass through the holes. For example, in a case where the silver ion capturing material 4 is made of a polymer, a network structure of the polymer provides the holes through which chloride ions can pass. This configuration allows the chloride ion to reach the reference electrode 3.

Moreover, according to the electrochemical measurement electrode of Embodiment 1-4, the silver ion capturing material 4 can be made of the material described in Embodiments 1-1-1 and 1-1-2. That is, the silver ion capturing material 4 can be made of a cation-exchange agent (Embodiment 1-1-1) or a cation adsorbent (Embodiment 1-1-2). With the use of these materials, it is possible to bring about an effect similar to those of Embodiments 1-1-1 and 1-1-2. The silver ion capturing material 4 can be made of a silver ion reducing agent (Embodiment 1-1-3), provided that the silver ion reducing agent is a compound having an aldehyde group. On the other hand, in a case where the silver ion reducing agent is a metal which has an ionization tendency higher than that of silver, the metal which is different from a material of the reference electrode 3 is to coat the surface of the reference electrode 3, and thereby the reference electrode 3 cannot accurately control the electric potential. Therefore, such a silver ion reducing agent made of a metal having the higher ionization tendency cannot be used as a material of the silver ion capturing material 4.

[Embodiment 1-5]

Figure 6:
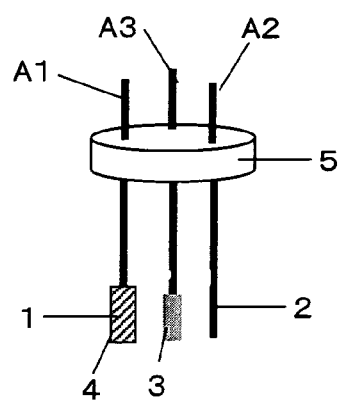
FIG. 6 is a perspective view schematically illustrating a structure of an electrochemical measurement electrode of Embodiment 1-5.

The following describes yet another modification of the configuration of Embodiment 1-1, with regard to the electrochemical measurement electrode of Embodiment 1. FIG. 6 is a perspective view schematically illustrating a structure of an electrochemical measurement electrode of the present Embodiment 1-5.

According to the electrochemical measurement electrode of Embodiment 1-5, the silver ion capturing material 4 is provided so as to cover the working electrode 1 (see FIG. 6). According to the electrochemical measurement electrode of Embodiment 1-5, the silver ion capturing material 4 covering the working electrode 1 is to eliminate a silver chloride complex ion before the silver chloride complex ion which is generated from the reference electrode 3 and emitted into the sample solution (in the measuring system) reaches the working electrode 1. This makes it possible to effectively eliminate the silver chloride complex ion before the silver chloride complex ion is reacted at the working electrode 1.

The silver ion capturing material 4 can eliminate the silver chloride complex ion as long as the silver ion capturing material 4 is provided so as to cover at least part of a surface of the working electrode 1. However, it is preferable that the silver ion capturing material 4 is provided so as to cover the whole surface of the working electrode 1 (see FIG. 6). This makes it possible to eliminate almost all the silver chloride complex ions which are to reach the working electrode 1.

Note that to "cover the whole surface of the working electrode 1" does not mean completely sealing the whole surface of the working electrode 1 with the silver ion capturing material 4 but means covering the working electrode 1 so that the electrochemical active substance in the sample solution can reach the working electrode 1. According to the configuration in which the silver ion capturing material 4 covers the whole surface of the working electrode 1, a hole are formed in the silver ion capturing material 4 so that electrochemical active substances can pass through the holes. For example, in a case where the silver ion capturing material 4 is made of a polymer, a network structure of the polymer provides the holes through which the electrochemical active substances can pass. This configuration allows the electrochemical active substance to reach the working electrode 1.

Moreover, according to the electrochemical measurement electrode of Embodiment 1-5, the silver ion capturing material 4 can be made of each of the materials described in Embodiments 1-1-1 and 1-1-2. That is, the silver ion capturing material 4 can be made of a cation-exchange agent (Embodiment 1-1-1) or a cation adsorbent (Embodiment 1-1-2). With the use of these materials, it is possible to bring about an effect similar to those of Embodiments 1-1-1 and 1-1-2. The silver ion capturing material 4 can be made of a silver ion reducing agent (Embodiment 1-1-3), provided that the silver ion reducing agent is a compound having an aldehyde group. On the other hand, in a case where the silver ion reducing agent is a metal which has an ionization tendency higher than that of silver, the metal which is different from a material of the working electrode 1 is to coat the surface of the working electrode 1, and thereby an accurate detection cannot be carried out because a property of the working electrode 1 itself is changed. Therefore, such a silver ion reducing agent made of a metal having the higher ionization tendency cannot be used as a material of the silver ion capturing material 4.

[Embodiment 1-6]

Figure 7:
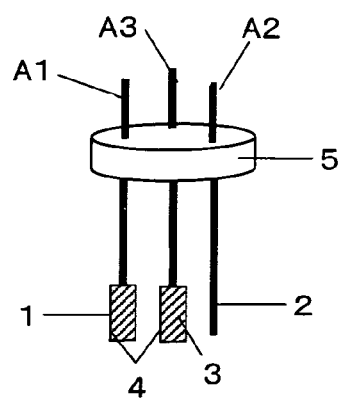
FIG. 7 is a perspective view schematically illustrating a structure of an electrochemical measurement electrode of Embodiment 1-6.

The following describes yet another modification of the configuration of Embodiment 1-1, with regard to the electrochemical measurement electrode of Embodiment 1. FIG. 7 is a perspective view schematically illustrating a structure of an electrochemical measurement electrode of the present Embodiment 1-6.

As shown in FIG. 7, according to the electrochemical measurement electrode of Embodiment 1-6, the silver ion capturing materials 4 are provided so as to cover the working electrode 1 and the reference electrode 3, respectively. The silver ion capturing material 4 which covers the reference electrode 3 has a configuration similar to that of Embodiment 1-4, and the silver ion capturing material 4 which covers the working electrode 1 has a configuration similar to that of Embodiment 1-5. Accordingly, explanations of the configurations are omitted here. Moreover, the respective silver ion capturing materials 4 which cover the reference electrode 3 and the working electrode 1 can be made of materials described in respective Embodiments 1-4 and 1-5. Accordingly, explanations of the materials are omitted here.

According to the electrochemical measurement electrode of Embodiment 1-6, silver chloride complex ions are to be eliminated by the silver ion capturing materials 4 (i) right after the silver chloride complex ions are generated from the reference electrode 3 and (ii) before the silver chloride complex ions reach the working electrode 1 after the silver chloride complex ions are emitted into the sample solution (the measuring system). This makes it possible to eliminate the silver chloride complex ions more effectively.

The following describes an electrochemical measuring method with the use of the electrochemical measurement electrode of Embodiment 1. The electrochemical measuring method includes the steps of: dipping the electrochemical measurement electrode in the sample solution, which contains an electrochemical active substance, so that the working electrode 1, the counter electrode 2, the reference electrode 3, and the silver ion capturing material 4 contact with the sample solution; and measuring the electrochemical active substance.

More specifically, first, the connection pads A1 through A3 of the electrochemical measurement electrode is connected to an electrochemical measuring device (e.g., a potentiostat). The connection pads A1 through A3 can be connected to the potentiostat, with the use of, for example, cords each of which has alligator clips on its both ends. Specifically, one end of each of the alligator clips pinches corresponding one of the connection pads A1 through A3 and the other end of each of the alligator clips pinches corresponding one of terminals of the potentiostat.

Then, the electrochemical measurement electrode is arranged so that the working electrode 1, the counter electrode 2, the reference electrode 3, and the silver ion capturing material 4 are dipped in the sample solution which is an object of an electrochemical measurement. With this arrangement, the electrochemical measurement is carried out.

The following describes a method for measuring p-aminophenol, as an example of the electrochemical measuring method with the use of the electrochemical measurement electrode of Embodiment 1.

As indicated by a formula below, when p-aminophenol is oxidized on the working electrode 1, p-quinonimine is generated.

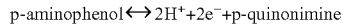

p-aminophenol $\leftrightarrow$ $2H^+ + 2e^- +$ p-quinonimine

An oxidation current generated in the oxidation is proportional to a concentration of the p-aminophenol. Therefore, it is possible to measure a concentration of the p-aminophenol in the sample solution by measuring the oxidation current with the use of an electrochemical measuring device such as a potentiostat.

Specifically, first, a calibration curve is prepared which indicates a relation between a concentration of p-aminophenol (pAP) and an oxidation current. Then, a measurement is carried out while the electrochemical measurement electrode is being dipped in the sample solution so that the working electrode 1, the counter electrode 2, the reference electrode 3, and the silver ion capturing material 4 are dipped in the sample solution. The oxidation current obtained by the measurement is compared with the calibration curve prepared in advance, and thereby the concentration of the p-aminophenol in the sample solution can be obtained.

Note that p-aminophenol is oxidized with an electric potential of 1 V or less. Accordingly, the p-aminophenol can be measured in an aqueous system. That is, the p-aminophenol is a material which is oxidized with an electric potential which can be measured in a range within which electrolysis of water does not occur.

Note that, in the above described example, the electrochemical measurement is carried out on the sample solution containing p-aminophenol as the electrochemical active substance. However, the electrochemical active substance which can be applied to the electrochemical measuring method of the present embodiment is not limited to the p-aminophenol. An electrochemical measurement similar to the above described measurement can be carried out on a substance such as potassium ferrocyanide, ferrocene, or a ferrocene derivative.

The ferrocene is a compound indicated as $Fe(C_5H_5)_2$, and can be indicated as the following chemical formula (1). In the chemical formula (1), an iron atom of the ferrocene is a divalent ion. Accordingly, the iron atom of the ferrocene is oxidized to a trivalent iron ion on the working electrode 1.

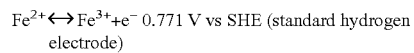

$Fe^{2+} \leftrightarrow Fe^{3+} + e^-$ 0.771 V vs SHE (standard hydrogen electrode)

In a molecule having a framework of the ferrocene, a redox reaction basically occurs. Therefore, the ferrocene derivative encompasses a compound in which at least one hydrogen atom in a cyclopentadienyl ring is substituted by another functional group.

The ferrocene itself does not dissolve in water. Accordingly, in a case where the ferrocene is used for a later described biosensor, it is preferable to use a derivative in which a water-soluble functional group is introduced in the ferrocene. Such a ferrocene derivative can be, for example, hydroxymethyl ferrocene (see a chemical formula (2)), or N,N,N-trimethylaminomethyl ferrocene (see a chemical formula (3)). Moreover, the ferrocene derivative can be a compound in which two or more identical functional groups are substituted (e.g., a compound indicated by a chemical formula (4)). A functional group introduced in the ferrocene is not limited to the functional groups shown in the chemical formulae (2) through (4), but can be another functional group as long as the functional group can give water solubility to the ferrocene.

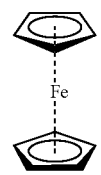

(1)

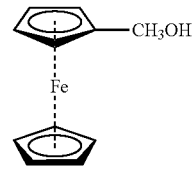

(2)

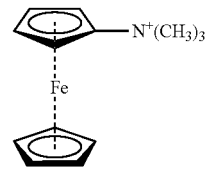

(3)

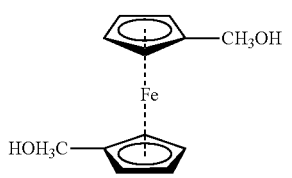

(4)

The electrochemical measurement electrode of Embodiment 1 can be used as a biosensor. The term "biosensor" indicates a sensor which measures a detection substance which is an object of a measurement based on a reaction of the detection substance and a biologically-relevant substance (e.g., an antibody, an enzyme, DNA, or a microbe). In general, such a biosensor can be, for example, an immune sensor, an enzyme sensor, or a microbial sensor.

The following describes an immunoanalytical method with the use of an immune sensor as the biosensor, as an example of an analysis method with the use of the electrochemical measurement electrode of Embodiment 1. Note that the electrochemical measurement electrode of Embodiment 1 can be applied to an analysis method with the use of the other biosensors described above for examples, as well as the analysis method with the use of the immune sensor. The immune sensor is used in an immunoanalytical method utilizing an antigen-antibody reaction. The immune sensor is useful in analysis and measurement methods in fields of medical treatment, biochemistry, and measuring allergen.

First, a reactive substance which specifically binds to a detection substance is fixed on the working electrode 1 of the electrochemical measurement electrode. The reactive substance can be, for example, protein such as an antibody, DNA, or a known substance such as peptide. In this example of the analysis method, an antibody which specifically binds to the detection substance is used as the reactive substance. A method for fixing the reactive substance on the working electrode 1 can be a known method employing: physical adsorption; covalent binding of the reactive substance and a functional group formed on the surface of the working electrode 1; or incorporation (entrapment) of protein with the use of a polymer material having a three-dimensional network structure. The reactive substance can be fixed on either part of the working electrode 1 or the whole surface of the working electrode 1. In order to prevent the detection substance from being nonspecifically adsorbed to the surface of the working electrode 1, it is preferable to prepare a nonspecific-adsorption-preventing film by treating the surface of the working electrode 1 with an aqueous albumin solution before dripping a sample solution.

Then, after the electrochemical measurement electrode is cleaned with a buffer solution, the sample solution containing the detection substance and an enzyme-labeled antibody is dripped. In this case, a complex containing an antibody, a detection substance, and an enzyme-labeled antibody is formed on the surface of the working electrode 1.

After the sample solution is dripped, the electrochemical measurement electrode is cleaned with the buffer solution, and then the electrochemical measurement electrode is dipped in a solution containing a substrate of a labeling enzyme so that an electrochemical measurement is carried out. The substrate has an electrochemical activity based on an activity of the labeling enzyme, and thereby the substrate causes an electrochemical reaction at the working electrode 1. The electrochemical reaction is detected and thereby a substrate concentration can be detected. Thus detected substrate concentration is synonymous with a concentration of the detection substance, and accordingly a target detection substance can be detected.

[Embodiment 2]
[Embodiment 2-1]

Figure 8:
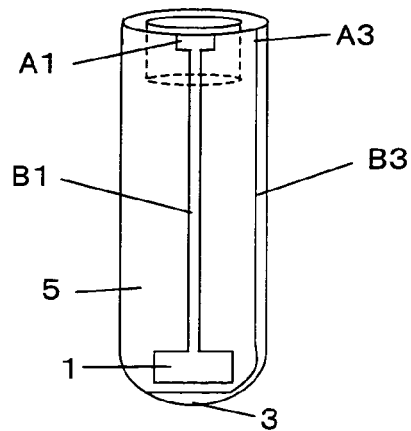
FIG. 8 is a view schematically illustrating a structure of an electrochemical measurement electrode of Embodiment 2-1: (a) is a front view, (b) is a rear view, and (c) is a bottom view.
Figure 8:
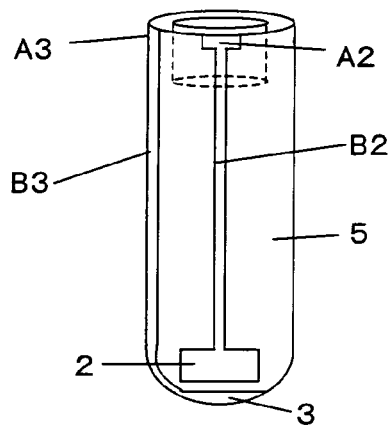
Figure 8:
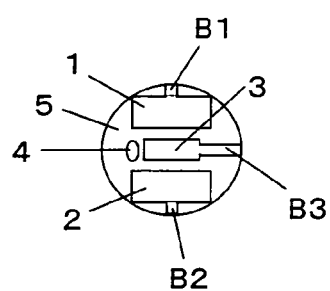

FIG. 8 is a view schematically illustrating a structure of an electrochemical measurement electrode of Embodiment 2-1. (a) of FIG. 8 is a front view, (b) of FIG. 8 is a rear view, and (c) of FIG. 8 is a bottom view. In this embodiment, a front side and a rear side are distinguished from each other for convenience of explanation. However, there is no distinction between front and rear in the actual electrochemical measurement electrode.

According to the electrochemical measurement electrode of Embodiment 2-1, an electrode holder 5 has a columnar shape with a convexed (bowl-shaped) bottom (see (a) through (c) of FIG. 8). Further, a working electrode 1, a counter electrode 2, and a reference electrode 3 are provided, side by side, on a surface of the convexed bottom of the electrode holder 5. Further, a silver ion capturing material 4 is provided on the surface of the convexed bottom of the electrode holder 5 and disposed closer to the reference electrode 3 than to the working electrode 1 and the counter electrode 2.

Further, leading electrode sections B1 through B3 are provided on a lateral face of the electrode holder 5. The leading electrode sections B1 through B3 extend, vertically in an upward direction of the electrode holder 5, from the working electrode 1, the counter electrode 2, and the reference electrode 3, respectively. Further, connection pads A1 through A3 are provide on respective apical ends (ends of the vertically upward direction, i.e., opposite ends to the bottom) of the leading electrode sections B1 through B3.

The electrode holder 5 is a base on which the working electrode 1, the counter electrode 2, the reference electrode 3, and the silver ion capturing material 4 are provided. According to the electrochemical measurement electrode shown in (a) through (c) of FIG. 8, the electrode holder 5 has the columnar shape with the convexed (bowl-shaped) bottom. However, the shape of the electrode holder 5 is not limited to a particular one, that is, the shape does not necessarily need to be the shape shown in FIG. 8. It is preferable that the electrode holder 5 has a bar-like shape such as a column, a square pole, or a triangle pole. Further, the electrode holder 5 has a hollowed section on top thereof so that alligator clips can pinch the top of the electrode holder 5 in order to connect the electrochemical measurement electrode with an electrochemical measuring device. A sidewall forming the hollowed section is concentric with the columnar shape of the electrode holder 5.

According to the electrochemical measurement electrode shown in (a) through (c) of FIG. 8, the working electrode 1 has a rectangular shape. However, the shape of the working electrode 1 is not limited to a particular one, that is, the shape does not necessarily need to have the shape shown in (a) through (c) of FIG. 8. The working electrode 1 can have, for example, a round shape, an elliptical shape, a half round shape, or any other shape. The working electrode 1 can be made of, for example, a conductive material such as metal, carbon, or graphite. The working electrode 1 can be provided on the surface of the electrode holder 5, for example, with a method such as a sputtering method, an evaporation method, or a printing method.

According to the electrochemical measurement electrode shown in (a) through (c) of FIG. 8, the counter electrode 2 has a rectangular shape, as with the working electrode 1. However, the shape of the counter electrode 2 is not limited to a particular one, that is, the shape does not necessarily need to be the shape shown in (a) through (c) of FIG. 8. The counter electrode 2 can have, for example, a round shape, an elliptical shape, a half round shape, or any other shape, as well as the rectangular shape. The counter electrode 2 can be provided so as to surround the working electrode 1. The counter electrode 2 is not limited in particular in terms of its size. However, it is preferable that the counter electrode 2 has a size which is at the same level as that of the working electrode 1 or has a size larger than that of the working electrode 1. This is because, in a case where the counter electrode 2 is far smaller than the working electrode 1, a current becomes difficult to flow and thereby an accurate electrochemical measurement cannot be carried out, since the counter electrode 2 is an electrode through which the current generated in the working electrode 1 flows. The counter electrode 2 can be made of a material which is similar to that of the working electrode 1. Moreover, the counter electrode 2 can be provided on the surface of the electrode holder 5 with a method similar to the above exemplified method for the working electrode 1.

According to the electrochemical measurement electrode shown in (a) through (c) of FIG. 8, connection pads A1 through A3 are provided in an upper part of the electrode holder 5. A position of each of the connection pads A1 through A3 can be set as appropriate in accordance with connection positions with the electrochemical measuring device, and the positions are not limited in particular as long as the respective connection pads A1 through A3 can connect the working electrode 1, the counter electrode 2, and the reference electrode 3 with the electrochemical measuring device. According to the electrochemical measurement electrode shown in (a) through (c) of FIG. 8, each of the connection pads A1 through A3 has a rectangular shape. However, the shape of each of the connection pads A1 through A3 is not limited to a particular one, that is, the shape does not necessarily need to be the shape shown in (a) through (c) of FIG. 8. The counter electrode 2 can have, for example, a round shape, an elliptical shape, a half round shape, or any other shape. Moreover, each of the connection pads A1 through A3 only needs to have a size with which the connection pads A1 through A3 can sufficiently contact with connection pads provided on the electrochemical measuring device. Each of the connection pads A1 through A3 can be made of a material which is similar to that of the working electrode 1 and the counter electrode 2. Moreover, each of the connection pads A1 through A3 can be provided on the surface of the electrode holder 5 with a method similar to the above exemplified method for the working electrode 1 and the counter electrode 2.

The leading electrode sections B1 through B3 are provided so as to connect the connection pads A1 through A3 with the working electrode 1, the counter electrode 2, and the reference electrode 3, respectively. According to the electrochemical measurement electrode shown in (a) through (c) of FIG. 8, each of the leading electrode sections B1 through B3 has a long and thin rectangular shape. However, the shape of each of the leading electrode sections B1 through B3 does not necessarily need to be the shape shown in (a) through (c) of FIG. 8, and the shape can be set arbitrarily. Each of the leading electrode sections B1 through B3 can have an arbitrary size. Each of the leading electrode sections B1 through B3 can be made of a material which is similar to that of the working electrode 1 and the counter electrode 2. Moreover, each of the leading electrode sections B1 through B3 can be provided on the surface of the electrode holder 5 with a method similar to the above exemplified method for the working electrode 1 and the counter electrode 2.

Note that configurations, which are not described above, of the electrochemical measurement electrode of Embodiment 2-1 are similar to those of the electrochemical measurement electrode of Embodiment 1-1-1. Accordingly, explanations for the configurations are omitted here.

According to the electrochemical measurement electrode of Embodiment 2-1, the silver ion capturing material 4 can be made of a material which is similar to those described in Embodiments 1-1-1 through 1-1-3. That is, the silver ion capturing material 4 can be made of a cation-exchange agent (Embodiment 1-1-1), a cation adsorbent (Embodiment 1-1-2), or a silver ion reducing agent (Embodiment 1-1-3). With the use of these materials, it is possible to bring about an effect similar to those of Embodiments 1-1-1 through 1-1-3.

[Embodiment 2-2]

Figure 9:
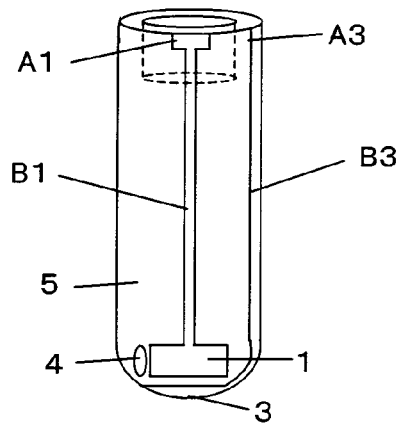
FIG. 9 is a view schematically illustrating a structure of an electrochemical measurement electrode of Embodiment 2-2: (a) is a front view, (b) is a rear view, and (c) is a bottom view.
Figure 9:
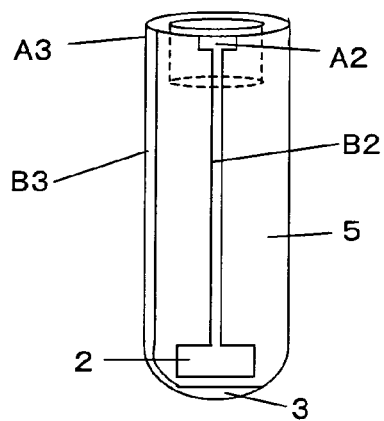
Figure 9:
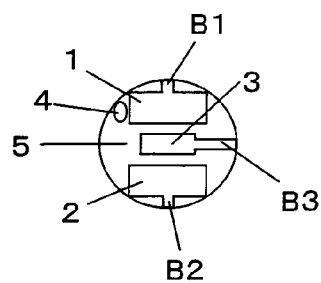

The following describes a modification of the configuration of Embodiment 2-1, with regard to the configuration of the electrochemical measurement electrode of Embodiment 2. FIG. 9 is a view schematically illustrating a structure of an electrochemical measurement electrode of Embodiment 2-2. (a) of FIG. 9 is a front view, (b) of FIG. 9 is a rear view, and (c) of FIG. 9 is a bottom view. In this embodiment, a front side and a rear side are distinguished from each other for convenience of explanation. However, there is no distinction between front and rear in the actual electrochemical measurement electrode. Note that, explanations are omitted here for configurations of the electrochemical measurement electrode of Embodiment 2-2 which are similar to those of the electrochemical measurement electrode of Embodiment 2-1.

According to the electrochemical measurement electrode of Embodiment 2-2, the silver ion capturing material 4 is provided in vicinity to the working electrode 1 (see (a) through (c) of FIG. 9). In other words, the silver ion capturing material 4 is disposed closer to the working electrode 1 than to the counter electrode 2 and the reference electrode 3.

According to the electrochemical measurement electrode of Embodiment 2-2, the silver chloride complex ion generated from the reference electrode 3 in the sample solution is to be eliminated by the silver ion capturing material 4 before the silver chloride complex ion reaches the working electrode 1 so as to cause an electrochemical reaction.

According to the electrochemical measurement electrode of Embodiment 2-2, the silver ion capturing material 4 can be made of a material which is similar to those described in Embodiments 1-1-1 through 1-1-3. That is, the silver ion capturing material 4 can be made of a cation-exchange agent (Embodiment 1-1-1), a cation adsorbent (Embodiment 1-1-2), or a silver ion reducing agent (Embodiment 1-1-3). With the use of these materials, it is possible to bring about an effect similar to those of Embodiments 1-1-1 through 1-1-3.

[Embodiment 2-3]

Figure 10:
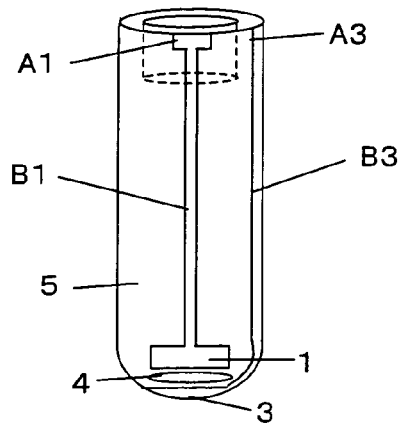
FIG. 10 is a view schematically illustrating a structure of an electrochemical measurement electrode of Embodiment 2-3: (a) is a front view, (b) is a rear view, and (c) is a bottom view.
Figure 10:
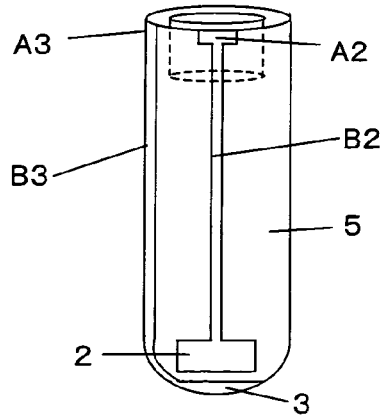
Figure 10:
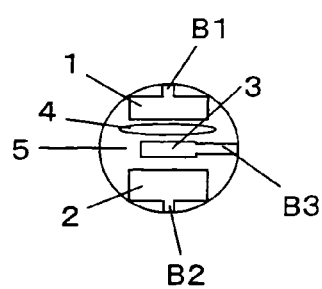

The following describes another modification of the configuration of Embodiment 2-1, with regard to the configuration of the electrochemical measurement electrode of Embodiment 2. FIG. 10 is a view schematically illustrating a structure of an electrochemical measurement electrode of Embodiment 2-3. (a) of FIG. 10 is a front view, (b) of FIG. 10 is a rear view, and (c) of FIG. 10 is a bottom view. In this embodiment, a front side and a rear side are distinguished from each other for convenience of explanation. However, there is no distinction between front and rear in the actual electrochemical measurement electrode. Note that explanations are omitted here for configurations of the electrochemical measurement electrode of Embodiment 2-3 which are similar to those of the electrochemical measurement electrode of Embodiment 2-1.

According to the electrochemical measurement electrode of Embodiment 2-3, the silver ion capturing material 4 is provided between the working electrode 1 and the reference electrode 3 (see (a) through (c) of FIG. 10).

According to the electrochemical measurement electrode of Embodiment 2-3, a silver chloride complex ion is eliminated by the silver ion capturing material 4 provided between the working electrode 1 and the reference electrode 3. This makes it possible to prevent the silver chloride complex ion, which is generated from the reference electrode 3 and emitted into the sample solution, from being diffused so as to reach the working electrode 1.

According to the electrochemical measurement electrode of Embodiment 2-3, the silver ion capturing material 4 can be made of a material which is similar to those described in Embodiments 1-1-1 through 1-1-3. That is, the silver ion capturing material 4 can be made of a cation-exchange agent (Embodiment 1-1-1), a cation adsorbent (Embodiment 1-1-2), or a silver ion reducing agent (Embodiment 1-1-3). With the use of these materials, it is possible to bring about an effect similar to those of Embodiments 1-1-1 through 1-1-3.

[Embodiment 2-4]

Figure 11:
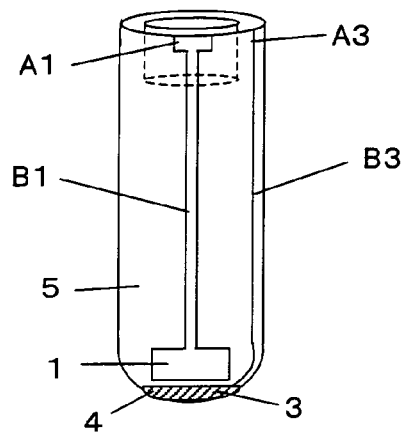
FIG. 11 is a view schematically illustrating a structure of an electrochemical measurement electrode of Embodiment 2-4: (a) is a front view, (b) is a rear view, and (c) is a bottom view.
Figure 11:
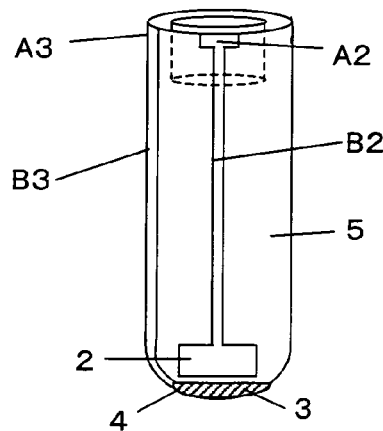
Figure 11:
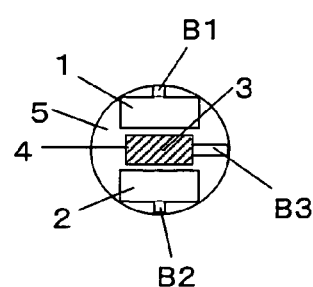

The following describes another modification of the configuration of Embodiment 2-1, with regard to the configuration of the electrochemical measurement electrode of Embodiment 2. FIG. 11 is a view schematically illustrating a structure of an electrochemical measurement electrode of Embodiment 2-4. (a) of FIG. 11 is a front view, (b) of FIG. 11 is a rear view, and (c) of FIG. 11 is a bottom view. In this embodiment, a front side and a rear side are distinguished from each other for convenience of explanation. However, there is no distinction between front and rear in the actual electrochemical measurement electrode. Note that explanations are omitted here for configurations of the electrochemical measurement electrode of Embodiment 2-4 which are similar to those of the electrochemical measurement electrode of Embodiment 2-1.

According to the electrochemical measurement electrode of Embodiment 2-4, the silver ion capturing material 4 is provided so as to cover the reference electrode 3 (see (a) through (c) of FIG. 11). According to the electrochemical measurement electrode of Embodiment 2-4, the silver ion capturing material 4 covering the reference electrode 3 eliminates a silver chloride complex ion right after the silver chloride complex ion is generated from the reference electrode 3. Therefore, the silver chloride complex ion is not emitted into the sample solution (in the measuring system) and thereby the silver chloride complex ion can be eliminated more effectively.

The silver ion capturing material 4 can eliminate the silver chloride complex ion as long as the silver ion capturing material 4 is provided so as to cover at least part of a surface of the reference electrode 3. However, it is preferable that the silver ion capturing material 4 is provided so as to cover the whole surface of the reference electrode 3 (see (c) of FIG. 11). This makes it possible to eliminate almost all the silver chloride complex ions generated from the reference electrode 3.

Moreover, according to the electrochemical measurement electrode of Embodiment 2-4, the silver ion capturing material 4 can be made of the material described in Embodiments 1-1-1 and 1-1-2. That is, the silver ion capturing material 4 can be made of a cation-exchange agent (Embodiment 1-1-1) or a cation adsorbent (Embodiment 1-1-2). With the use of these materials, it is possible to bring about an effect similar to those of Embodiments 1-1-1 and 1-1-2. The silver ion capturing material 4 can be made of a silver ion reducing agent (Embodiment 1-1-3), provided that the silver ion reducing agent is a compound having an aldehyde group. On the other hand, in a case where the silver ion reducing agent is a metal which has an ionization tendency higher than that of silver, the metal which is different from a material of the reference electrode 3 is to coat the surface of the reference electrode 3, and thereby the reference electrode 3 cannot accurately control the electric potential. Therefore, such a silver ion reducing agent made of a metal having the higher ionization tendency cannot be used as a material of the silver ion capturing material 4.

[Embodiment 2-5]

Figure 12:
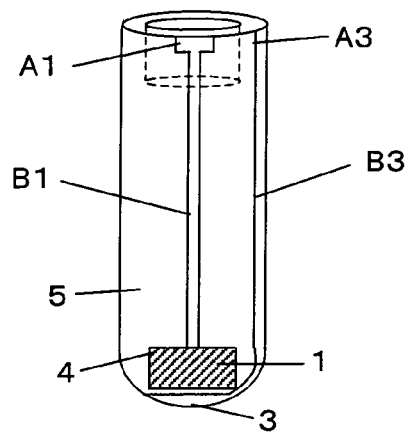
FIG. 12 is a view schematically illustrating a structure of an electrochemical measurement electrode of Embodiment 2-5: (a) is a front view, (b) is a rear view, and (c) is a bottom view.
Figure 12:
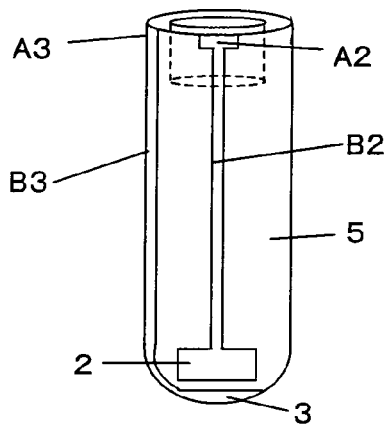
Figure 12:
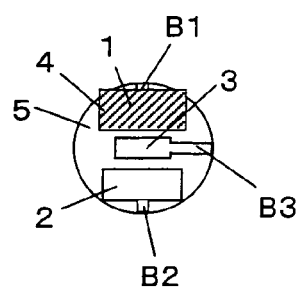

The following describes another modification of the configuration of Embodiment 2-1, with regard to the configuration of the electrochemical measurement electrode of Embodiment 2. FIG. 12 is a view schematically illustrating a structure of an electrochemical measurement electrode of Embodiment 2-5. (a) of FIG. 12 is a front view, (b) of FIG. 12 is a rear view, and (c) of FIG. 12 is a bottom view. In this embodiment, a front side and a rear side are distinguished from each other for convenience of explanation. However, there is no distinction between front and rear in the actual electrochemical measurement electrode. Note that explanations are omitted here for configurations of the electrochemical measurement electrode of Embodiment 2-5 which are similar to those of the electrochemical measurement electrode of Embodiment 2-1.

According to the electrochemical measurement electrode of Embodiment 2-5, the silver ion capturing material 4 is provided so as to cover the working electrode 1 (see (a) through (c) of FIG. 12). According to the electrochemical measurement electrode of Embodiment 2-5, the silver ion capturing material 4 covering the working electrode 1 is to eliminate a silver chloride complex ion before the silver chloride complex ion which is generated from the reference electrode 3 and emitted into the sample solution (in the measuring system) reaches the working electrode 1. This makes it possible to effectively eliminate the silver chloride complex ion before the silver chloride complex ion is reacted at the working electrode 1.

The silver ion capturing material 4 can eliminate the silver chloride complex ion as long as the silver ion capturing material 4 is provided so as to cover at least part of a surface of the working electrode 1. However, it is preferable that the silver ion capturing material 4 is provided so as to cover the whole surface of the working electrode 1 (see (c) of FIG. 12). This makes it possible to eliminate almost all the silver chloride complex ions which are to reach the working electrode 1.

Moreover, according to the electrochemical measurement electrode of Embodiment 2-5, the silver ion capturing material can be made of each of the material described in Embodiments 1-1-1 and 1-1-2. That is, the silver ion capturing material 4 can be made of a cation-exchange agent (Embodiment 1-1-1) or a cation adsorbent (Embodiment 1-1-2). With the use of these materials, it is possible to bring about an effect similar to those of Embodiments 1-1-1 and 1-1-2. The silver ion capturing material 4 can be made of a silver ion reducing agent (Embodiment 1-1-3), provided that the silver ion reducing agent is a compound having an aldehyde group. On the other hand, in a case where the silver ion reducing agent is a metal which has an ionization tendency higher than that of silver, the metal which is different from a material of the working electrode 1 is to coat the surface of the working electrode 1, and thereby an accurate detection cannot be carried out because a property of the working electrode 1 itself is changed. Therefore, such a silver ion reducing agent made of a metal having the higher ionization tendency cannot be used as a material of the silver ion capturing material 4.

[Embodiment 2-6]

Figure 13:
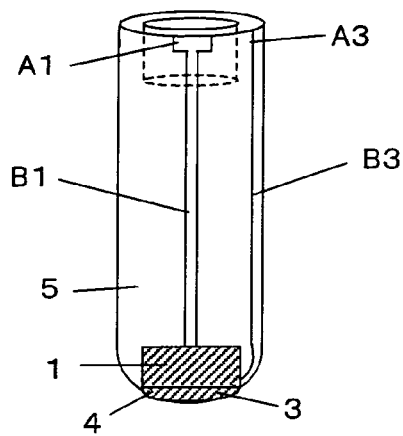
FIG. 13 is a view schematically illustrating a structure of an electrochemical measurement electrode of Embodiment 2-6: (a) is a front view, (b) is a rear view, and (c) is a bottom view.
Figure 13:
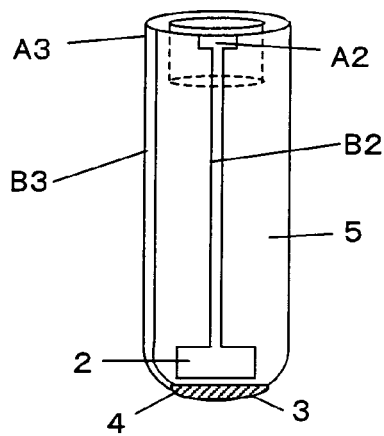
Figure 13:
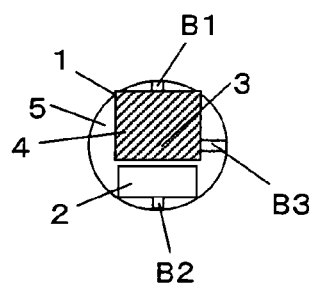

The following describes yet another modification of the configuration of Embodiment 2-1, with regard to the configuration of the electrochemical measurement electrode of Embodiment 2. FIG. 13 is a view schematically illustrating a structure of an electrochemical measurement electrode of Embodiment 2-6. (a) of FIG. 13 is a front view, (b) of FIG. 13 is a rear view, and (c) of FIG. 13 is a bottom view. In this embodiment, a front side and a rear side are distinguished from each other for convenience of explanation. However, there is no distinction between front and rear in the actual electrochemical measurement electrode. Note that explanations are omitted here for the configurations of the electrochemical measurement electrode of Embodiment 2-6 which are similar to those of the electrochemical measurement electrode of Embodiment 2-1.

As shown in (a) through (c) of FIG. 13, according to the electrochemical measurement electrode of Embodiment 2-6, the silver ion capturing materials 4 are provided so as to cover the working electrode 1 and the reference electrode 3, respectively. The silver ion capturing material 4 which covers the reference electrode 3 has a configuration similar to that of Embodiment 2-4, and the silver ion capturing material 4 which covers the working electrode 1 has a configuration similar to that of Embodiment 2-5. Accordingly, explanations of the configurations are omitted here. Moreover, the respective silver ion capturing materials 4 which cover the reference electrode 3 and the working electrode 1 can be made of materials described in respective Embodiments 2-4 and 2-5. Accordingly, explanations of the materials are omitted here.

According to the electrochemical measurement electrode of Embodiment 2-6, silver chloride complex ions are to be eliminated by the silver ion capturing materials 4 (i) right after the silver chloride complex ions are generated from the reference electrode 3 and (ii) before the silver chloride complex ions reach the working electrode 1 after the silver chloride complex ions are emitted into the sample solution (the measuring system). This makes it possible to eliminate the silver chloride complex ions more effectively.

An electrochemical measuring method with the use of the electrochemical measurement electrode of each of Embodiments 2-1 through 2-6 can be carried out in a similar way to the electrochemical measuring method described in Embodiment 1. Accordingly, an explanation for the electrochemical measuring method is omitted here.

The electrochemical measurement electrode of each of Embodiments 2-1 through 2-6 can be used as a biosensor, as with Embodiment 1. An analysis method with the use of the electrochemical measurement electrode of each of Embodiments 2-1 through 2-6 can be carried out in a similar way to the analysis method described in Embodiment 1. Accordingly, an explanation for the analysis method is omitted here.

[Embodiment 3]
[Embodiment 3-1]

Figure 14:
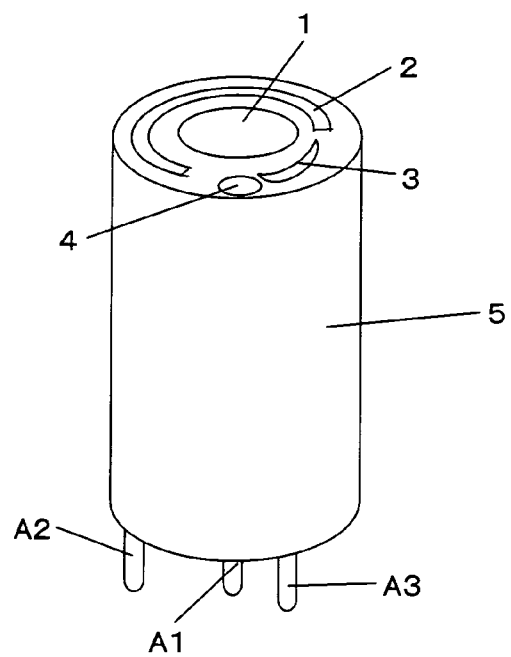
FIG. 14 is a view schematically illustrating a structure of an electrochemical measurement electrode of Embodiment 3-1: (a) is a perspective view illustrating an appearance of the electrochemical measurement electrode, and (b) is a perspective view illustrating an internal structure of the electrochemical measurement electrode.
Figure 14:
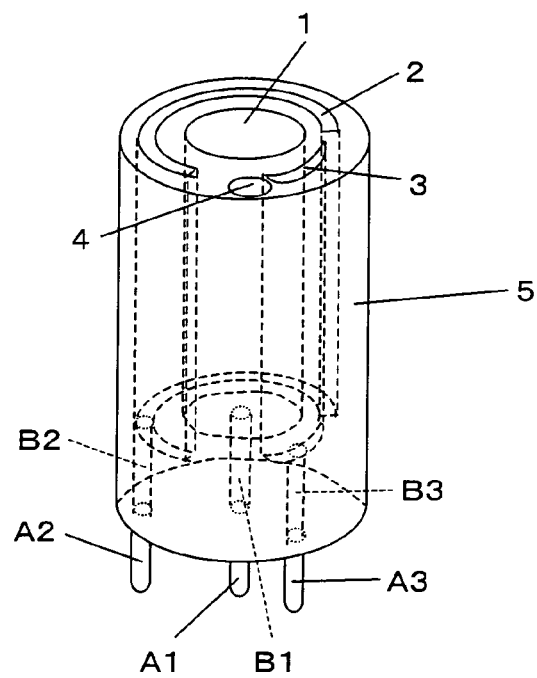

FIG. 14 is a view schematically illustrating a structure of an electrochemical measurement electrode of Embodiment 3-1. (a) of FIG. 14 is a perspective view illustrating an appearance of the electrochemical measurement electrode, and (b) of FIG. 14 is a perspective view illustrating an internal structure of the electrochemical measurement electrode.

According to the electrochemical measurement electrode of Embodiment 3-1, an electrode holder 5 has a columnar shape (see (a) and (b) of FIG. 14). Further, a working electrode 1, a counter electrode 2, and a reference electrode 3 are embedded in the electrode holder 5. The working electrode 1, the counter electrode 2, and the reference electrode 3 are arranged in parallel with an axial direction of the columnar-shaped electrode holder 5 so as to be exposed on only one of edge faces in the axial direction of the electrode holder 5. Note that, in the following descriptions, the edge face on which the working electrode 1, the counter electrode 2, and the reference electrode 3 are exposed is referred to as an upper face, and an edge face opposite to the upper face is referred to as a lower face.

Leading electrode sections B1 through B3 are provided inside the electrode holder 5 so that the respective leading electrode sections B1 through B3 extend from the working electrode 1, the counter electrode 2, and the reference electrode 3 toward the lower face along the axial direction. Further, electrode pads A1 through A3 are provided on lower ends of the respective leading electrode sections B1 through B3 so that the electrode pads A1 through A3 protrude in the axial direction from the lower face of the electrode holder 5. According to the electrochemical measurement electrode of Embodiment 3-1, each of the electrode pads A1 through A3 is pinched by an alligator clip or the like so that the electrochemical measurement electrode is connected to an electrochemical measuring device.

Further, a silver ion capturing material 4 is provided on the upper face of the electrode holder 5 at a position closer to the reference electrode 3 than to the working electrode 1 and the counter electrode 2.

According to the electrochemical measurement electrode of Embodiment 3-1, the leading electrode sections B1 through B3 are provided inside the electrode holder 5, and thereby the leading electrode sections B1 through B3 do not contact with a sample solution. The working electrode 1, the counter electrode 2, and the reference electrode 3 are to contact with the sample solution via their exposed parts on the upper face of the electrode holder 5. Therefore, an electrochemical measurement can be carried out while an effective electrode area of each of the working electrode 1, the counter electrode 2, and the reference electrode 3 is constantly kept stabilized. This makes it possible to improve accuracy in a measurement.

Note that configurations of the electrochemical measurement electrode of Embodiment 3-1 which are not described above are similar to those of the electrochemical measurement electrodes of Embodiment 1-1-1 and Embodiment 2-1. Accordingly, explanations for the configurations are omitted here.

According to the electrochemical measurement electrode of Embodiment 3-1, the silver ion capturing material 4 can be made of a material which is similar to those described in Embodiments 1-1-1 through 1-1-3. That is, the silver ion capturing material 4 can be made of a cation-exchange agent (Embodiment 1-1-1), a cation adsorbent (Embodiment 1-1-2), or a silver ion reducing agent (Embodiment 1-1-3). With the use of these materials, it is possible to bring about an effect similar to those of Embodiments 1-1-1 through 1-1-3.

[Embodiment 3-2]

Figure 15:
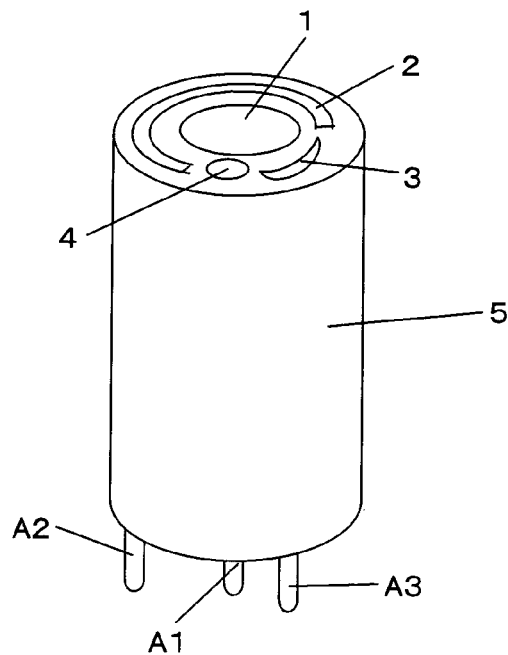
FIG. 15 is a perspective view illustrating an appearance of an electrochemical measurement electrode of Embodiment 3-2.

The following describes a modification of the configuration of Embodiment 3-1, with regard to the configuration of the electrochemical measurement electrode of Embodiment 3. FIG. 15 is a perspective view illustrating an appearance of an electrochemical measurement electrode of Embodiment 3-2. Note that, the electrochemical measurement electrode of Embodiment 3-2 has an internal structure which is similar to that of the electrochemical measurement electrode of Embodiment 3-1. Accordingly, an explanation for the internal structure is omitted here.

According to the electrochemical measurement electrode of Embodiment 3-2, the silver ion capturing material 4 is provided in vicinity to the working electrode 1 (see FIG. 15), as with Embodiment 1-2 and Embodiment 2-2. In other words, the silver ion capturing material 4 is disposed closer to the working electrode 1 than to the counter electrode 2 and the reference electrode 3. Therefore, the electrochemical measurement electrode of Embodiment 3-2 can bring about an effect similar to those of Embodiment 1-2 and Embodiment 2-2.

[Embodiment 3-3]

Figure 16:
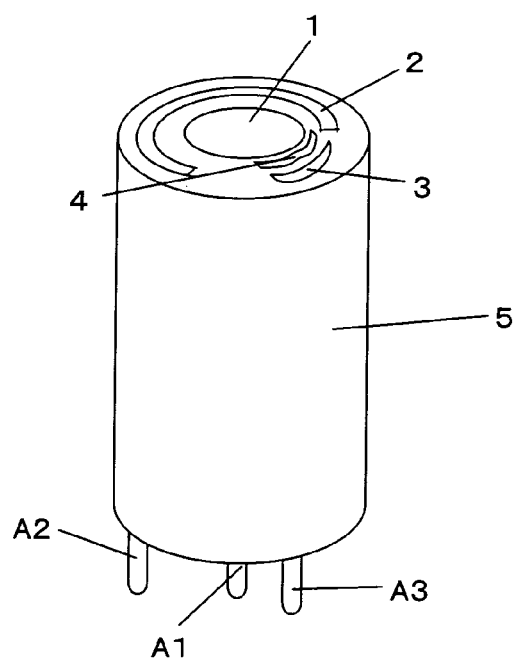
FIG. 16 is a perspective view illustrating an appearance of an electrochemical measurement electrode of Embodiment 3-3.

The following describes another modification of the configuration of Embodiment 3-1, with regard to the configuration of the electrochemical measurement electrode of Embodiment 3. FIG. 16 is a perspective view illustrating an appearance of an electrochemical measurement electrode of Embodiment 3-3. Note that, the electrochemical measurement electrode of Embodiment 3-3 has an internal structure which is similar to that of the electrochemical measurement electrode of Embodiment 3-1. Accordingly, an explanation for the internal structure is omitted here.

According to the electrochemical measurement electrode of Embodiment 3-3, the silver ion capturing material 4 is provided between the working electrode 1 and the reference electrode 3 (see FIG. 16), as with Embodiment 1-3 and Embodiment 2-3. Therefore, the electrochemical measurement electrode of Embodiment 3-3 can bring about an effect similar to those of Embodiment 1-3 and Embodiment 2-3.

[Embodiment 3-4]

Figure 17:
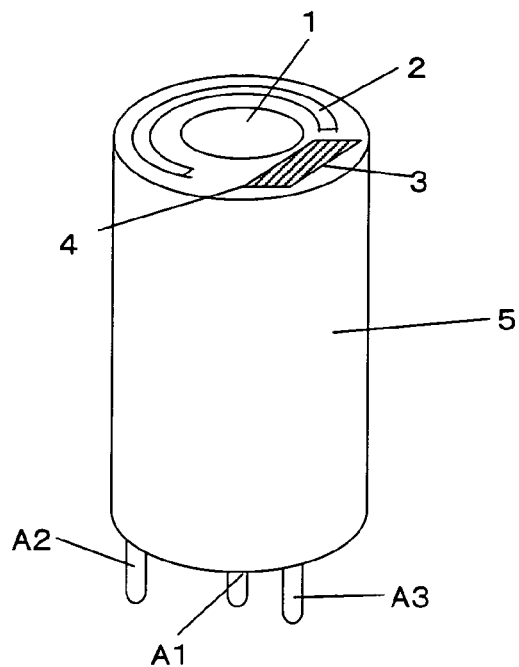
FIG. 17 is a perspective view illustrating an appearance of an electrochemical measurement electrode of Embodiment 3-4.

The following describes yet another modification of the configuration of Embodiment 3-1, with regard to the configuration of the electrochemical measurement electrode of Embodiment 3. FIG. 17 is a perspective view illustrating an appearance of an electrochemical measurement electrode of Embodiment 3-4. Note that, the electrochemical measurement electrode of Embodiment 3-4 has an internal structure which is similar to that of the electrochemical measurement electrode of Embodiment 3-1. Accordingly, an explanation for the internal structure is omitted here.

According to the electrochemical measurement electrode of Embodiment 3-4, the silver ion capturing material 4 is provided so as to cover the reference electrode 3 (see FIG. 17), as with Embodiment 1-4 and Embodiment 2-4. Therefore, the electrochemical measurement electrode of Embodiment 3-4 can bring about an effect similar to those of Embodiment 1-4 and Embodiment 2-4.

[Embodiment 3-5]

Figure 18:
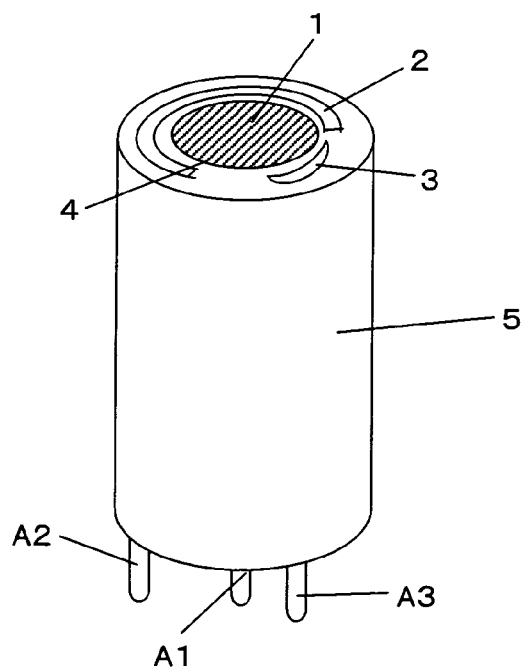
FIG. 18 is a perspective view illustrating an appearance of an electrochemical measurement electrode of Embodiment 3-5.

The following describes yet another modification of the configuration of Embodiment 3-1, with regard to the configuration of the electrochemical measurement electrode of Embodiment 3. FIG. 18 is a perspective view illustrating an appearance of an electrochemical measurement electrode of Embodiment 3-5. Note that, the electrochemical measurement electrode of Embodiment 3-5 has an internal structure which is similar to that of the electrochemical measurement electrode of Embodiment 3-1. Accordingly, an explanation for the internal structure is omitted here.

According to the electrochemical measurement electrode of Embodiment 3-5, the silver ion capturing material 4 is provided so as to cover the working electrode 1 (see FIG. 18), as with Embodiment 1-5 and Embodiment 2-5. Therefore, the electrochemical measurement electrode of Embodiment 3-5 can bring about an effect similar to those of Embodiment 1-5 and Embodiment 2-5.

[Embodiment 3-6]

Figure 19:
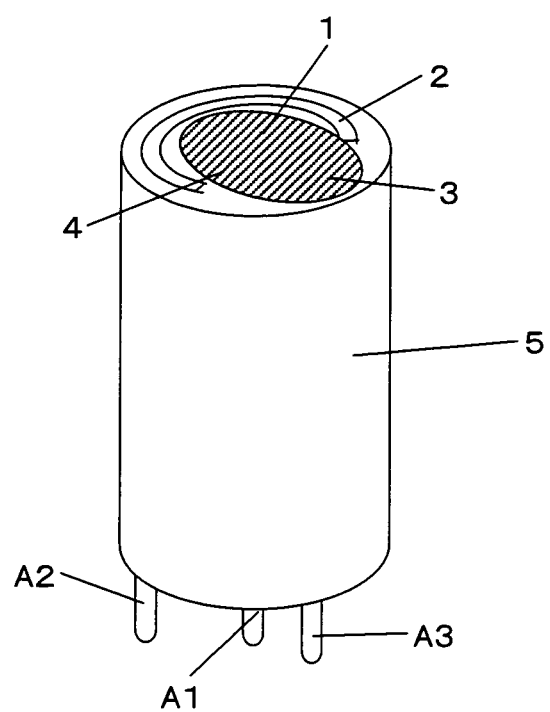
FIG. 19 is a perspective view illustrating an appearance of an electrochemical measurement electrode of Embodiment 3-6.

The following describes yet another modification of the configuration of Embodiment 3-1, with regard to the configuration of the electrochemical measurement electrode of Embodiment 3. FIG. 19 is a perspective view illustrating an appearance of an electrochemical measurement electrode of Embodiment 3-6. Note that, the electrochemical measurement electrode of Embodiment 3-6 has an internal structure which is similar to that of the electrochemical measurement electrode of Embodiment 3-1. Accordingly, an explanation for the internal structure is omitted here.

According to the electrochemical measurement electrode of Embodiment 3-6, the silver ion capturing material 4 is provided so as to cover both the working electrode 1 and the reference electrode 3 (see FIG. 19), as with Embodiment 1-6 and Embodiment 2-6. Therefore, the electrochemical measurement electrode of Embodiment 3-6 can bring about an effect similar to those of Embodiment 1-6 and Embodiment 2-6.

An electrochemical measuring method with the use of the electrochemical measurement electrode of Embodiments 3-1 through 3-6 can be carried out in a similar way to the electrochemical measuring method described in Embodiment 1. According to each of the electrochemical measurement electrodes of Embodiments 3-1 through 3-6, the silver ion capturing material 4 is provided on the upper face of the electrode holder 5, and the working electrode 1, the counter electrode 2, and the reference electrode 3 are exposed only on the upper face of the electrode holder 5. Therefore, it is possible to drip a sample solution on the upper face of the electrode holder 5 so that the working electrode 1, the counter electrode 2, the reference electrode 3, and the silver ion capturing material 4 are dipped in the sample solution.

Each of the electrochemical measurement electrodes of Embodiments 3-1 through 3-6 can be used as a biosensor, as with Embodiment 1. An analysis method with the use of the electrochemical measurement electrode of Embodiments 3-1 through 3-6 can be carried out in a similar way to the analysis method described in Embodiment 1. Note that, according to the analysis method with the use of the electrochemical measurement electrode of any of Embodiments 3-1 through 3-6, a detection substance can be measured by dripping a substrate solution containing labeling enzyme on a surface of the electrochemical measurement electrode, as well as dipping the electrochemical measurement electrode in the substrate solution.

[Embodiment 4]

[Embodiment 4-1]

Figure 20:
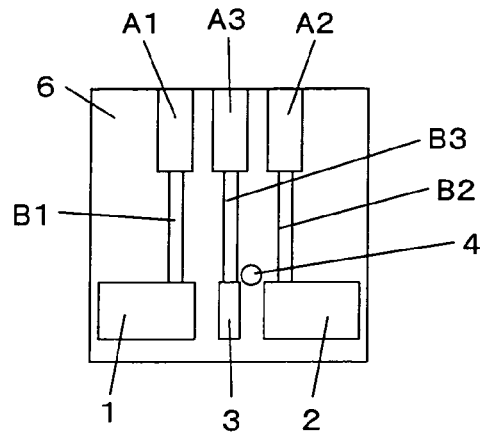
FIG. 20 is a top view schematically illustrating a structure of an electrochemical measurement electrode of Embodiment 4-1.

FIG. 20 is a top view schematically illustrating a structure of an electrochemical measurement electrode of Embodiment 4-1. According to the electrochemical measurement electrode of Embodiment 4-1, a working electrode 1, a counter electrode 2, a reference electrode 3, and a silver ion capturing material 4 are provided on an insulating substrate 6 (see FIG. 20). When viewed from above, the insulating substrate 6 has a rectangular shape. The working electrode 1, the counter electrode 2, and the reference electrode 3 are disposed side by side on one of edge parts of the insulating substrate 6. Further, connection pads A1 through A3 are provided on the other one of edge parts of the insulating substrate 6 opposite to the edge part in which the working electrode 1, the counter electrode 2, and the reference electrode 3 are disposed. Leading electrode sections B1 through B3 are provided so as to connect the connection pads A1 through A3 with the working electrode 1, the counter electrode 2, and the reference electrode 3, respectively.

The silver ion capturing material 4 is provided in vicinity to the reference electrode 3 in the insulating substrate 6. That is, the silver ion capturing material 4 is disposed closer to the reference electrode 3 than to the working electrode 1 and the counter electrode 2.

According to the electrochemical measurement electrode of Embodiment 4-1, the working electrode 1, the counter electrode 2, and the reference electrode 3 are provided compactly on the insulating substrate 6. This brings about an advantageous effect of reducing an amount of a sample solution used for an electrochemical measurement. Moreover, it is possible to produce an electrochemical measurement electrode by (i) forming the working electrode 1, the counter electrode 2, the reference electrode 3, the connection pads A1 through A3, and the leading electrode sections B1 through B3 by patterning an surface of the insulating substrate 6, and dividing the patterned insulating substrate 6 into each section. Accordingly, the electrochemical measurement electrode can be produced in large quantities.

According to the electrochemical measurement electrode shown in FIG. 20, the insulating substrate 6 has a rectangular planar shape. However, the planar shape of the insulating substrate 6 is not limited to a particular one, that is, the planar shape does not necessarily need to be the shape shown in FIG. 20. Moreover, the insulating substrate 6 can be made of, for example, an insulation material such as glass, quartz, ceramics, or plastic.

Note that configurations of the electrochemical measurement electrode of Embodiment 4-1 which are not described above are similar to those of the electrochemical measurement electrodes of Embodiment 1-1-1 and Embodiment 2-1. Accordingly, explanations for the configurations are omitted here.

According to the electrochemical measurement electrode of Embodiment 4-1, the silver ion capturing material 4 can be made of a material which is similar to those described in Embodiments 1-1-1 through 1-1-3. That is, the silver ion capturing material 4 can be made of a cation-exchange agent (Embodiment 1-1-1), a cation adsorbent (Embodiment 1-1-2), or a silver ion reducing agent (Embodiment 1-1-3). With the use of these materials, it is possible to bring about an effect similar to those of Embodiments 1-1-1 through 1-1-3.

[Embodiment 4-2]

Figure 21:
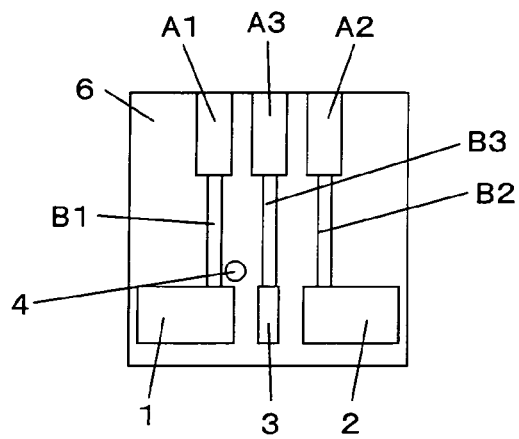
FIG. 21 is a top view schematically illustrating a structure of an electrochemical measurement electrode of Embodiment 4-2.

The following describes a modification of the configuration of Embodiment 4-1, with regard to the configuration of the electrochemical measurement electrode of Embodiment 4. FIG. 21 is a top view schematically illustrating a structure of an electrochemical measurement electrode of Embodiment 4-2. Note that, explanations are omitted here for the configurations of the electrochemical measurement electrode of Embodiment 4-2 which are similar to those of the electrochemical measurement electrode of Embodiment 4-1.

According to the electrochemical measurement electrode of Embodiment 4-2, the silver ion capturing material 4 is provided in vicinity to the working electrode 1 (see FIG. 21), as with Embodiment 1-2, Embodiment 2-2, and Embodiment 3-2. In other words, the silver ion capturing material 4 is disposed closer to the working electrode 1 than to the counter electrode 2 and the reference electrode 3. Therefore, the electrochemical measurement electrode of Embodiment 4-2 can bring about an effect similar to those of Embodiment 1-2, Embodiment 2-2, and Embodiment 3-2.

[Embodiment 4-3]

Figure 22:
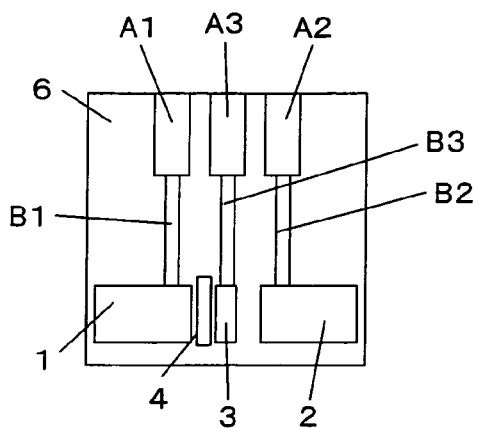
FIG. 22 is a top view schematically illustrating a structure of an electrochemical measurement electrode of Embodiment 4-3.

The following describes another modification of the configuration of Embodiment 4-1, with regard to the configuration of the electrochemical measurement electrode of Embodiment 4. FIG. 22 is a top view schematically illustrating a structure of an electrochemical measurement electrode of Embodiment 4-3. Note that explanations are omitted here for the configurations of the electrochemical measurement electrode of Embodiment 4-3 which are similar to those of the electrochemical measurement electrode of Embodiment 4-1.

According to the electrochemical measurement electrode of Embodiment 4-3, the silver ion capturing material 4 is provided between the working electrode 1 and the reference electrode 3 (see FIG. 22), as with Embodiment 1-3, Embodiment 2-3, and Embodiment 3-3. Therefore, the electrochemical measurement electrode of Embodiment 4-3 can bring about an effect similar to those of Embodiment 1-3, Embodiment 2-3, and Embodiment 3-3.

[Embodiment 4-4]

Figure 23:
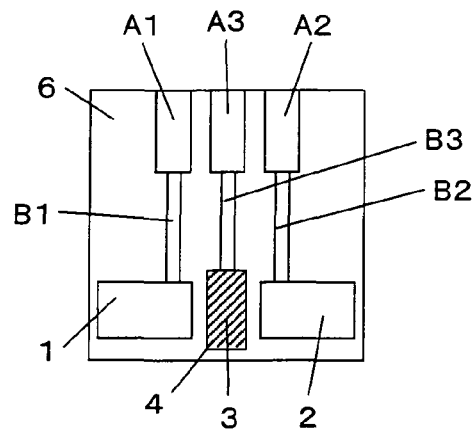
FIG. 23 is a top view schematically illustrating a structure of an electrochemical measurement electrode of Embodiment 4-4.

The following describes yet another modification of the configuration of Embodiment 4-1, with regard to the configuration of the electrochemical measurement electrode of Embodiment 4. FIG. 23 is a top view schematically illustrating a structure of an electrochemical measurement electrode of Embodiment 4-4. Note that explanations are omitted here for the configurations of the electrochemical measurement electrode of Embodiment 4-4 which are similar to those of the electrochemical measurement electrode of Embodiment 4-1.

According to the electrochemical measurement electrode of Embodiment 4-4, the silver ion capturing material 4 is provided so as to cover the reference electrode 3 (see FIG. 23), as with Embodiment 1-4, Embodiment 2-4, and Embodiment 3-4. Therefore, the electrochemical measurement electrode of Embodiment 4-4 can bring about an effect similar to those of Embodiment 1-4, Embodiment 2-4, and Embodiment 3-4.

[Embodiment 4-5]

Figure 24:
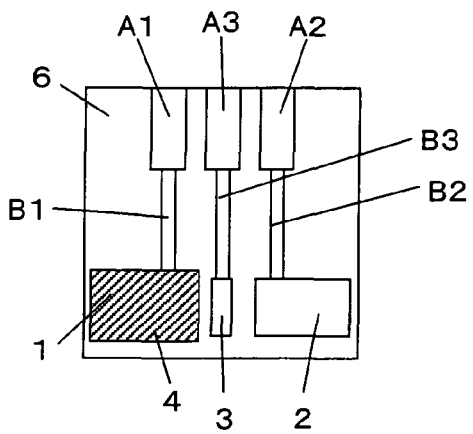
FIG. 24 is a top view schematically illustrating a structure of an electrochemical measurement electrode of Embodiment 4-5.

The following describes yet another modification of the configuration of Embodiment 4-1, with regard to the configuration of the electrochemical measurement electrode of Embodiment 4. FIG. 24 is a top view schematically illustrating a structure of an electrochemical measurement electrode of Embodiment 4-5. Note that, regarding configurations of the electrochemical measurement electrode of Embodiment 4-5 which are similar to those of the electrochemical measurement electrode of Embodiment 4-1, explanations for the configurations are omitted here.

According to the electrochemical measurement electrode of Embodiment 4-5, the silver ion capturing material 4 is provided so as to cover the working electrode 1 (see FIG. 24), as with Embodiment 1-5, Embodiment 2-5, and Embodiment 3-5. Therefore, the electrochemical measurement electrode of Embodiment 4-5 can bring about an effect similar to those of Embodiment 1-5, Embodiment 2-5, and Embodiment 3-5.

[Embodiment 4-6]

Figure 25:
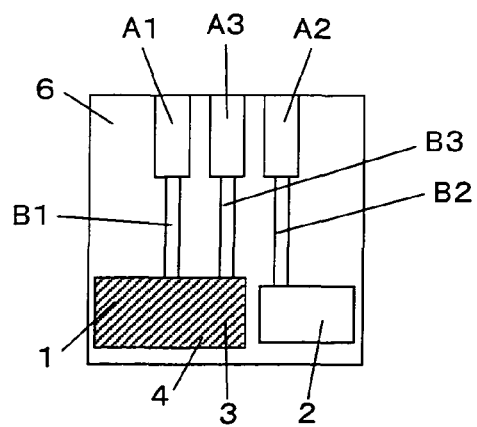
FIG. 25 is a top view schematically illustrating a structure of an electrochemical measurement electrode of Embodiment 4-6.

The following describes yet another modification of the configuration of Embodiment 4-1, with regard to the configuration of the electrochemical measurement electrode of Embodiment 4. FIG. 25 is a top view schematically illustrating a structure of an electrochemical measurement electrode of Embodiment 4-6. Note that explanations are omitted here for the configurations of the electrochemical measurement electrode of Embodiment 4-6 which are similar to those of the electrochemical measurement electrode of Embodiment 4-1.

According to the electrochemical measurement electrode of Embodiment 4-6, the silver ion capturing material 4 is provided so as to cover both the working electrode 1 and the reference electrode 3 (see FIG. 25), as with Embodiment 1-6, Embodiment 2-6, and Embodiment 3-6. Therefore, the electrochemical measurement electrode of Embodiment 4-6 can bring about an effect similar to those of Embodiment 1-6, Embodiment 2-6, and Embodiment 3-6.

The following describes an electrochemical measuring method with the use of the electrochemical measurement electrode of Embodiment 4. The electrochemical measuring method includes the steps of (i) dripping a sample solution containing an electrochemical active substance on the working electrode 1, the counter electrode 2, the reference electrode 3, and the silver ion capturing material 4 and (ii) measuring the electrochemical active substance.

More specifically, first, the electrochemical measurement electrode is connected to an electrochemical measuring device (e.g., a potentiostat) with the use of the connection pads A1 through A3. Then, the sample solution which is an object of the electrochemical measurement is dripped on the working electrode 1, the counter electrode 2, the reference electrode 3, and the silver ion capturing material 4, and the measurement is carried out.

Moreover, the electrochemical measurement electrode of Embodiment 4 can be used as a biosensor. The following describes an example of an analysis method with the use of the electrochemical measurement electrode of Embodiment 4, where an immunoanalytical method is carried out with the use of an immune sensor as the biosensor.

First, a reactive substance which specifically binds to a detection substance is fixed on the working electrode 1 of the electrochemical measurement electrode. The reactive substance can be, for example, protein such as an antibody, DNA, or a known substance such as peptide. In this example of the analysis method, an antibody which specifically binds to the detection substance is used as the reactive substance. A method for fixing the reactive substance on the working electrode 1 can be a known method employing: physical adsorption; covalent binding of the reactive substance and a functional group formed on the surface of the working electrode 1; or incorporation (entrapment) of protein with the use of a polymer material having a three-dimensional network structure. The reactive substance can be fixed on either part of the working electrode 1 or the whole surface of the working electrode 1. In order to prevent the detection substance from being nonspecifically adsorbed to the surface of the working electrode 1, it is preferable to prepare a nonspecific-adsorption-preventing film by treating the surface of the working electrode 1 with an aqueous albumin solution before dripping a sample solution.

Then, after the electrochemical measurement electrode is cleaned with a buffer solution, the sample solution containing the detection substance and an enzyme-labeled antibody is dripped. In this case, a complex containing an antibody, a detection substance, and an enzyme-labeled antibody is formed on the surface of the working electrode 1.

After the sample solution is dripped, the electrochemical measurement electrode is cleaned with the buffer solution, and then the electrochemical measurement electrode is dipped in a solution containing a substrate of a labeling enzyme so that an electrochemical measurement is carried out. The substrate has an electrochemical activity based on an activity of the labeling enzyme, and thereby the substrate causes an electrochemical reaction at the working electrode 1. The electrochemical reaction is detected and thereby a substrate concentration can be detected. Thus detected substrate concentration is synonymous with a concentration of the detection substance, and accordingly a target detection substance can be detected.

[Embodiment 5]

[Embodiment 5-1]

Figure 26:
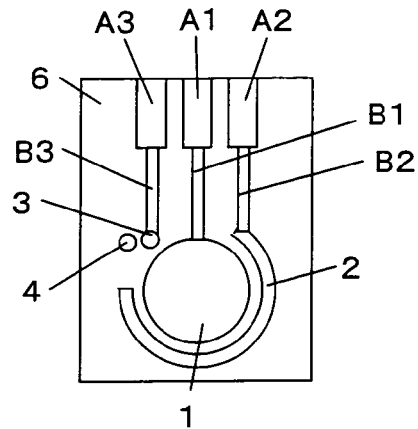
FIG. 26 is a top view schematically illustrating a structure of an electrochemical measurement electrode of Embodiment 5-1.

FIG. 26 is a top view schematically illustrating a structure of an electrochemical measurement electrode of Embodiment 5-1. According to the electrochemical measurement electrode of Embodiment 5-1, a working electrode 1, a counter electrode 2, a reference electrode 3, and a silver ion capturing material 4 are provided on an insulating substrate 6 (see FIG. 26). When viewed from above, the insulating substrate 6 has a rectangular shape. The working electrode 1 provided on the insulating substrate 6 has a round shape when viewed from above. The counter electrode 2 is provided so as to partially surround the working electrode 1. The reference electrode 3 is provided in vicinity to a part of the working electrode 1 which part is not surrounded by the counter electrode 2. According to the electrochemical measurement electrode of Embodiment 5-1, the reference electrode 3 is not disposed between the working electrode 1 and the counter electrode 2.

Note that, according to the electrochemical measurement electrode shown in FIG. 26, the working electrode 1 has the round shape. However, the shape of the working electrode 1 is not limited to a particular one, that is, the shape does not necessarily need to be the shape shown in FIG. 26. The working electrode 1 can have any shape such as an elliptical shape, a half round shape, or a rectangular shape.

According to the electrochemical measurement electrode of Embodiment 5-1, the counter electrode 2 and the reference electrode 3 are disposed close to the working electrode 1 so as to surround the working electrode 1 having the round shape. This makes it possible to provide the electrochemical measurement electrode which is smaller in size.

Note that configurations of the electrochemical measurement electrode of Embodiment 5-1 which are not described above are similar to those of the electrochemical measurement electrode of Embodiment 4-1. Accordingly, explanations for the configurations are omitted here.

According to the electrochemical measurement electrode of Embodiment 5-1, the silver ion capturing material 4 can be made of a material which is similar to those described in Embodiments 1-1-1 through 1-1-3. That is, the silver ion capturing material 4 can be made of a cation-exchange agent (Embodiment 1-1-1), a cation adsorbent (Embodiment 1-1-2), or a silver ion reducing agent (Embodiment 1-1-3). With the use of these materials, it is possible to bring about an effect similar to those of Embodiments 1-1-1 through 1-1-3.

[Embodiment 5-2]

Figure 27:
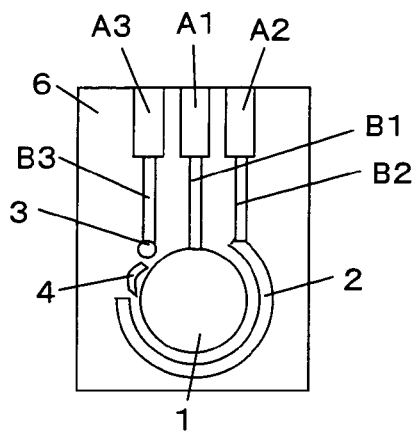
FIG. 27 is a top view schematically illustrating a structure of an electrochemical measurement electrode of Embodiment 5-2.

The following describes a modification of the configuration of Embodiment 5-1, with regard to the configuration of the electrochemical measurement electrode of Embodiment 5. FIG. 27 is a top view schematically illustrating a structure of an electrochemical measurement electrode of Embodiment 5-2. Note that explanations are omitted here for the configurations of the electrochemical measurement electrode of Embodiment 5-2 which are similar to those of the electrochemical measurement electrode of Embodiment 5-1.

According to the electrochemical measurement electrode of Embodiment 5-2, the silver ion capturing material 4 is provided in vicinity to the working electrode 1 (see FIG. 27), as with Embodiment 1-2, Embodiment 2-2, Embodiment 3-2, and Embodiment 4-2. In other words, the silver ion capturing material 4 is disposed closer to the working electrode 1 than to the counter electrode 2 and the reference electrode 3. Therefore, the electrochemical measurement electrode of Embodiment 5-2 can bring about an effect similar to those of Embodiment 1-2, Embodiment 2-2, Embodiment 3-2, and Embodiment 4-2.

[Embodiment 5-3]

Figure 28:
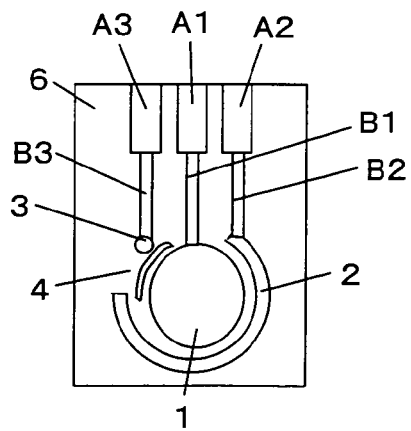
FIG. 28 is a top view schematically illustrating a structure of an electrochemical measurement electrode of Embodiment 5-3.

The following describes another modification of the configuration of Embodiment 5-1, with regard to the configuration of the electrochemical measurement electrode of Embodiment 5. FIG. 28 is a top view schematically illustrating a structure of an electrochemical measurement electrode of Embodiment 5-3. Note that explanations are omitted here for the configurations of the electrochemical measurement electrode of Embodiment 5-3 which are similar to those of the electrochemical measurement electrode of Embodiment 5-1.

According to the electrochemical measurement electrode of Embodiment 5-3, the silver ion capturing material 4 is provided between the working electrode 1 and the reference electrode 3 (see FIG. 28), as with Embodiment 1-3, Embodiment 2-3, Embodiment 3-3, and Embodiment 4-3. Therefore, the electrochemical measurement electrode of Embodiment 5-3 can bring about an effect similar to those of Embodiment 1-3, Embodiment 2-3, Embodiment 3-3, and Embodiment 4-3.

[Embodiment 5-4]

Figure 29:
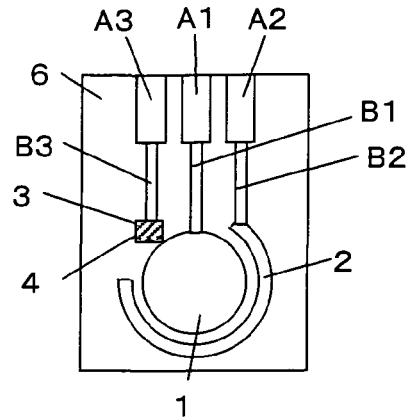
FIG. 29 is a top view schematically illustrating a structure of an electrochemical measurement electrode of Embodiment 5-4.

The following describes yet another modification of the configuration of Embodiment 5-1, with regard to the configuration of the electrochemical measurement electrode of Embodiment 5. FIG. 29 is a top view schematically illustrating a structure of an electrochemical measurement electrode of Embodiment 5-4. Note that explanations are omitted here for the configurations of the electrochemical measurement electrode of Embodiment 5-4 which are similar to those of the electrochemical measurement electrode of Embodiment 5-1.

According to the electrochemical measurement electrode of Embodiment 5-4, the silver ion capturing material 4 is provided so as to cover the reference electrode 3 (see FIG. 29), as with Embodiment 1-4, Embodiment 2-4, Embodiment 3-4, and Embodiment 4-4. Therefore, the electrochemical measurement electrode of Embodiment 5-4 can bring about an effect similar to those of Embodiment 1-4, Embodiment 2-4, Embodiment 3-4, and Embodiment 4-4.

[Embodiment 5-5]

Figure 30:
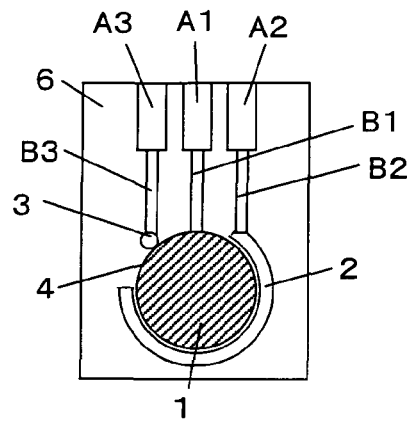
FIG. 30 is a top view schematically illustrating a structure of an electrochemical measurement electrode of Embodiment 5-5.

The following describes yet another modification of the configuration of Embodiment 5-1, with regard to the configuration of the electrochemical measurement electrode of Embodiment 5. FIG. 30 is a top view schematically illustrating a structure of an electrochemical measurement electrode of Embodiment 5-5. Note that explanations are omitted here for the configurations of the electrochemical measurement electrode of Embodiment 5-5 which are similar to those of the electrochemical measurement electrode of Embodiment 5-1.

According to the electrochemical measurement electrode of Embodiment 5-5, the silver ion capturing material 4 is provided so as to cover the working electrode 1 (see FIG. 30), as with Embodiment 1-5, Embodiment 2-5, Embodiment 3-5, and Embodiment 4-5. Therefore, the electrochemical measurement electrode of Embodiment 5-5 can bring about an effect similar to those of Embodiment 1-5, Embodiment 2-5, Embodiment 3-5, and Embodiment 4-5.

[Embodiment 5-6]

Figure 31:
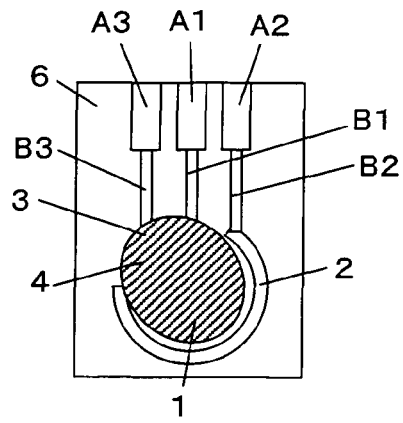
FIG. 31 is a top view schematically illustrating a structure of an electrochemical measurement electrode of Embodiment 5-6.

The following describes yet another modification of the configuration of Embodiment 5-1, with regard to the configuration of the electrochemical measurement electrode of Embodiment 5. FIG. 31 is a top view schematically illustrating a structure of an electrochemical measurement electrode of Embodiment 5-6. Note that explanations are omitted here for the configurations of the electrochemical measurement electrode of Embodiment 5-6 which are similar to those of the electrochemical measurement electrode of Embodiment 5-1.

According to the electrochemical measurement electrode of Embodiment 5-6, the silver ion capturing material 4 is provided so as to cover both the working electrode 1 and the reference electrode 3 (see FIG. 31), as with Embodiment 1-6, Embodiment 2-6, Embodiment 3-6, and Embodiment 4-6. Therefore, the electrochemical measurement electrode of Embodiment 5-6 can bring about an effect similar to those of Embodiment 1-6, Embodiment 2-6, Embodiment 3-6, and Embodiment 4-6.

An electrochemical measuring method with the use of the electrochemical measurement electrode of any of Embodiments 5-1 through 5-6 can be carried out in a similar way to the electrochemical measuring method described in Embodiment 4. Accordingly, an explanation of the electrochemical measuring method is omitted here.

Moreover, the electrochemical measurement electrode of Embodiments 5-1 through 5-6 can be used as a biosensor, as with Embodiment 4. An analysis method with the use of the electrochemical measurement electrode of any of Embodiments 5-1 through 5-6 can be carried out in a similar way to the analysis method described in Embodiment 4. Accordingly, an explanation for the analysis method is omitted here.

[Embodiment 6]

Figure 32:
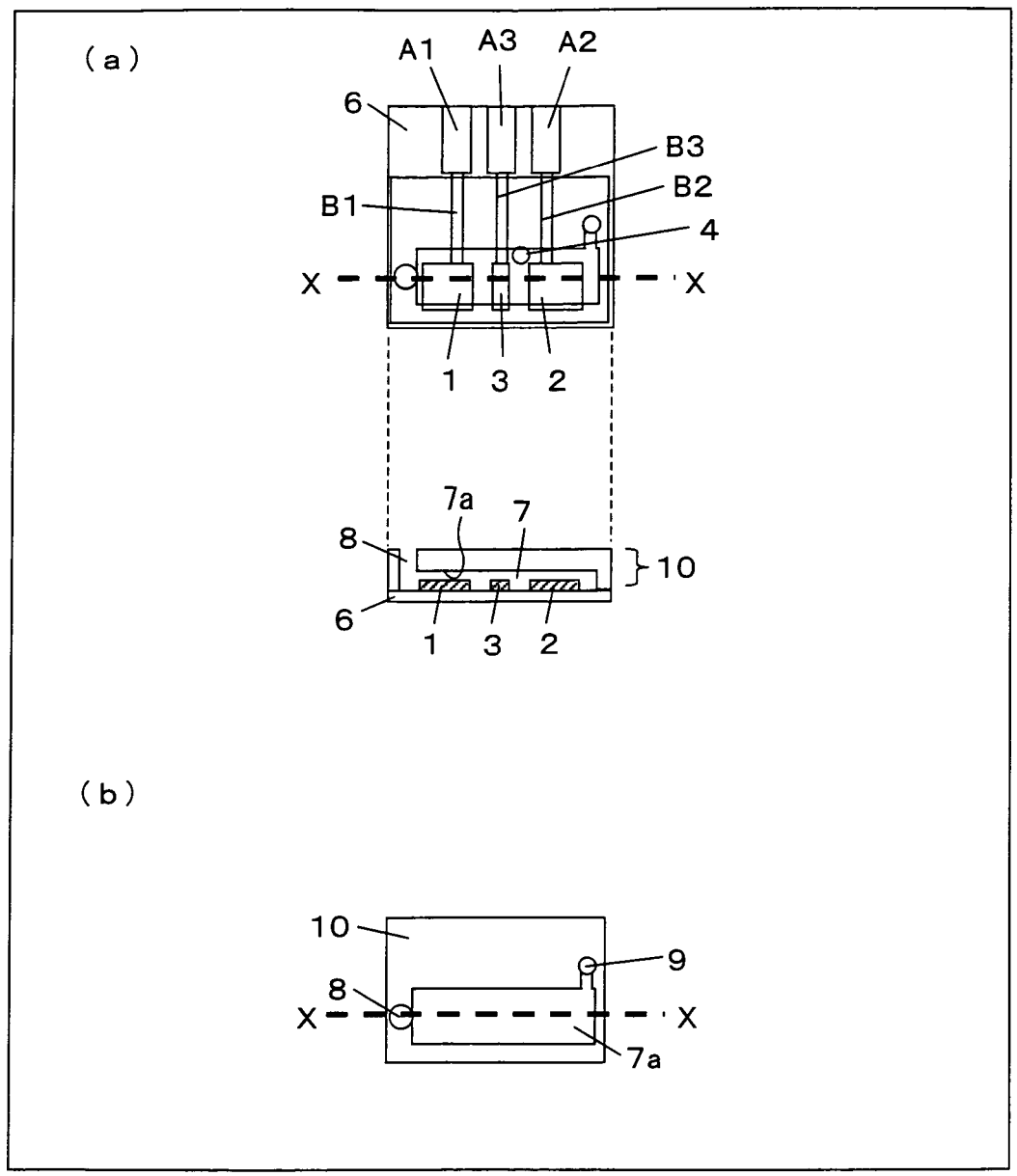
FIG. 32 is a view schematically illustrating a structure of an electrochemical measurement electrode chip of Embodiment 6: (a) is a top view and a cross sectional view taken along the line X-X' in the top view and (b) is a top view schematically illustrating a structure of a microchip which partially constitutes the electrochemical measurement electrode chip.

According to an electrochemical measurement electrode chip of the present embodiment, a microchip is attached to the electrochemical measurement electrode of any of Embodiments 4 and 5. The microchip has a hollowed section 7a which confines a working electrode 1, a counter electrode 2, and a reference electrode 3 therein. In the electrochemical measurement electrode chip, the hollowed section 7a and an insulating substrate 6 defines an area which is referred to as a measurement section 7. The following describes the electrochemical measurement electrode chip of the present embodiment with reference to (a) and (b) of FIG. 32. FIG. 32 is a view schematically illustrating a structure of an electrochemical measurement electrode chip of the present embodiment. (a) of FIG. 32 is a top view and a cross sectional view taken along the line X-X' in the top view and (b) of FIG. 32 is a top view schematically illustrating a structure of a microchip which is included in the electrochemical measurement electrode chip. Note that, (a) and (b) of FIG. 32 illustrate a configuration including the electrochemical measurement electrode of Embodiment 4-1. Accordingly, an explanation for the electrochemical measurement electrode is omitted here.

As shown in (a) and (b) of FIG. 32, the microchip includes a chip substrate 10 in which the hollowed section 7a, an inlet section 8, and an outlet section 9 are formed. Moreover, as shown in the cross-section of (a) of FIG. 32, the measurement section 7 is an area defined by the hollowed section 7a and the insulating substrate 6. The inlet section 8 and the outlet section 9 are holes which penetrate an upper plane (i.e., a bottom plane of the hollowed section 7a) forming the measurement section 7. According to (a) and (b) of FIG. 32, the chip substrate 10 has a rectangular planar shape. However, the shape of the chip substrate 10 is not limited to a particular one, that is, the shape does not necessarily need to be the shape shown in (a) and (b) of FIG. 32. It is preferable that the chip substrate 10 has a thickness of approximately 0.1 to 5 mm. Moreover, the chip substrate 10 can be made of a material such as glass, quartz, ceramics, or plastic.

The hollowed section 7a forming the measurement section 7 is formed so that its bottom plane covers the working electrode 1, the counter electrode 2, and the reference electrode 3 when the chip substrate 10 is attached to the electrochemical measurement electrode. According to the electrochemical measurement electrode chip of the present embodiment, a sample solution is to be supplied into an area defined by the hollowed section 7a and the insulating substrate 6 (i.e., in the measurement section 7). The measurement section 7 defines an area in which an electrochemical reaction of the sample solution is caused. According to (a) and (b) of FIG. 32, sidewalls forming the measurement section 7 form a rectangular shape. However, the shape formed by the sidewalls is not limited to a particular one, that is, the shape does not necessarily need to be the shape shown in (a) and (b) of FIG. 32. An area of the upper plane of the measurement section 7 (i.e., the bottom plane of the hollowed section 7a) only needs to be large enough to cover the working electrode 1, the counter electrode 2, and the reference electrode 3 made of silver and silver chloride. A cross-sectional shape, which is perpendicular to a substrate face of the chip substrate 10, of the measurement section 7 (shown in the cross-sectional view in (a) of FIG. 32) is not limited in particular, as long as the sample solution can flow in the measurement section 7. The cross-sectional shape of the measurement section 7 can be any shape such as a round shape, an elliptical shape, a half round shape, or a rectangular shape. Moreover, it is preferable that a depth of the measurement section 7 (i.e., a height of the sidewall surrounding the hollowed section 7a) is approximately 1 µm through 1 mm.

The inlet section 8 is formed in order to feed the sample solution into the microchip and is connected to the measurement section 7. A cross-sectional shape of the inlet section 8 is not limited in particular. The cross-sectional shape of the inlet section 8 can be a round shape, an elliptical shape, a polygonal shape, or any other shape. Moreover, the inlet section 8 has a cross-sectional width of 1 µm or more.

The outlet section 9 is formed in order to discharge the sample solution outside the microchip. Note that, when the sample solution is being fed, the outlet section 9 serves as an air hole. A cross-sectional shape of the outlet section 9 is not limited in particular. The cross-sectional shape of the outlet section 9 can be a round shape, an elliptical shape, a polygonal shape, or any other shape. Moreover, the outlet section 9 has a cross-sectional width of 1 µm or more.

According to the electrochemical measurement electrode chip of the present embodiment, the sample solution is to be fed in the area (measurement section 7) defined by the hollowed section 7a and the insulating substrate 6. This makes it possible to reduce an amount of the sample solution. Further, a reduction of measurement time and simplification of analysis operation can be achieved. As a result, an accurate and efficient electrochemical measurement can be realized.

The microchip is produced by forming the hollowed section 7a and openings corresponding to the inlet section 8 and the outlet section 9 in the chip substrate 10. A method for forming the measurement section 7, etc. in the chip substrate 10 is not limited in particular. The method can be, for example, (i) a mechanical processing with the use of a microdrill, etc. or (ii) a formation with a chemical treatment such as etching. Alternatively, the measurement section 7, etc. can be formed by hardening a light-curing resin or a thermosetting resin which has been poured into a mold in which patterns of the sections are formed. It is also possible that, the formation of the measurement section 7, etc. can be carried out by hot-embossing a substrate material made of a polyolefin resin, a polymethacrylic resin, or a polycarbonate resin, with the use of a mold in which patterns of the sections are formed.

Note that, according to the configuration shown in (a) and (b) of FIG. 32, the electrochemical measurement electrode chip includes the electrochemical measurement electrode of Embodiment 4-1. However, the electrochemical measurement electrode chip of the present embodiment is not limited to the configuration shown in (a) and (b) of FIG. 32. The electrochemical measurement electrode chip of the present embodiment can includes the electrochemical measurement electrode of any of Embodiments 4-2 through 4-6 and Embodiments 5-1 through 5-6.

[Embodiment 7]

Figure 33:
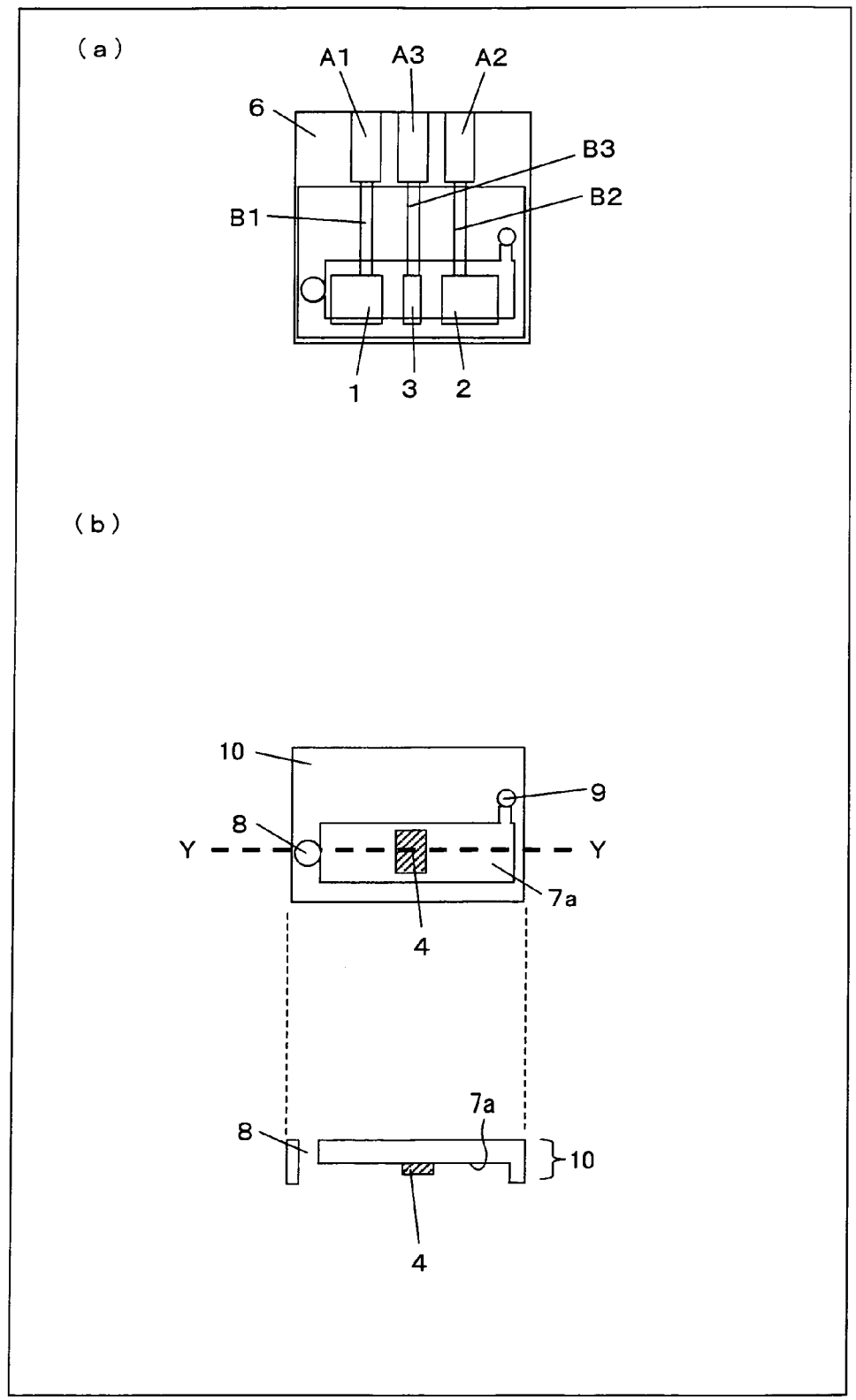
FIG. 33 is a view schematically illustrating a structure of an electrochemical measurement electrode chip of Embodiment 7: (a) is a top view and (b) is a top view schematically illustrating a structure of a microchip which partially constitutes the electrochemical measurement electrode chip and a cross sectional view taken along the line Y-Y' in the top view.

The following describes an electrochemical measurement electrode chip of the present embodiment with reference to (a) and (b) of FIG. 33. FIG. 33 is a view schematically illustrating a structure of an electrochemical measurement electrode chip of the present embodiment. (a) of FIG. 33 is a top view and (b) of FIG. 33 is a top view schematically illustrating a structure of a microchip which is included in the electrochemical measurement electrode chip, and a cross sectional view taken along the line Y-Y' in the top view.

According to the electrochemical measurement electrode chip of the present embodiment, a microchip is attached to an electrochemical measurement electrode, as with that of Embodiment 6. This makes it possible to reduce an amount of a sample solution. Further, a reduction of measurement time and simplification of analysis operation can be achieved. As a result, an accurate and efficient electrochemical measurement can be realized.

In the electrochemical measurement electrode chip of the present embodiment, the silver ion capturing material 4 is provided in a position which is different from that of Embodiment 6. According to the electrochemical measurement electrode chip of the present embodiment, the silver ion capturing material 4 is provided on a microchip side, not on an electrochemical measurement electrode side (see the cross-sectional view of (b) of FIG. 33). Specifically, the silver ion capturing material 4 is provided on the bottom plane of the hollowed section 7a in the microchip. Note that the silver ion capturing material 4 can be provided on either part of a surface forming the hollowed section 7a or the whole surface forming the hollowed section 7a. Alternatively, the silver ion capturing material 4 can be provided on a sidewall forming the hollowed section 7a.

The following describes an electrochemical measuring method with the use of the electrochemical measurement electrode chip of any of Embodiments 6 and 7. The electrochemical measuring method includes the steps of: feeding a sample solution containing an electrochemical active substance via the inlet section 8 so as to fill the measurement section 7 with the sample solution; and measuring the electrochemical active substance.

The electrochemical measurement electrode chip of any of Embodiments 6 and 7 can be used as a biosensor.

The electrochemical measurement electrode chip of any of Embodiment 6 and 7 can be used as a biosensor, as with the electrochemical measurement electrode of any of Embodiments 1 through 5. It is possible to carry out an antibody immobilization, formation of a nonspecific-adsorption film, reaction of sample solution, and a cleaning either (i) in the electrochemical measurement electrode chip or (ii) before the microchip is attached to the electrochemical measurement electrode. A substrate solution is fed into the electrochemical measurement electrode chip and a measurement is carried out. This makes it possible to reduce an amount of the solution and time, as compared with the measurement with the use of the electrochemical measurement electrode.

According to Embodiments 1 through 7, the silver ion capturing material 4 is provided in the electrochemical measurement electrode or the electrochemical measurement electrode chip. However, the silver ion capturing material 4 can be dispersed in the sample solution for achieving a similar effect.

As described above, the electrochemical measurement electrode of the present invention includes a silver ion capturing material which captures a silver ion out of a silver chloride complex ion generated from the reference electrode.

As described above, the electrochemical measurement electrode chip of the present invention includes: the above described electrochemical measurement electrode; and a microchip which covers the electrochemical measurement electrode, the microchip having (i) a hollowed section which contains therein the working electrode and the reference electrode and (ii) an inlet section via which the sample solution is fed into a measurement section which is an area defined by the electrochemical measurement electrode and the hollowed section.

The electrochemical measuring method of the present invention uses the above described electrochemical measurement electrode and includes the steps of: dipping the electrochemical measurement electrode in the sample solution containing the chloride ion and the electrochemical active substance, the electrochemical measurement electrode being dipped so that, at least partially, each of the working electrode, the reference electrode, and the silver ion capturing material contacts with the sample solution; and measuring the electrochemical active substance in the sample solution.

The electrochemical measuring method of the present invention uses the above described electrochemical measurement electrode chip and includes the steps of: feeding the sample solution containing the chloride ion and the electrochemical active substance into the measurement section via the inlet section; and measuring the electrochemical active substance in the sample solution.

The analysis method of the present invention (i) uses an electrochemical measurement electrode which includes a working electrode on which a reactive substance which specifically reacts with a detection substance is at least partially fixed and (ii) includes the steps of: dipping the electrochemical measurement electrode in the sample solution containing the detection substance, the electrochemical measurement electrode being dipped so that, at least partially, each of the working electrode, the reference electrode, and the silver ion capturing material contacts with the sample solution; and measuring, under the presence of the chloride ion, the electrochemical active substance generated in a reaction of the reactive substance and the detection substance.

The analysis method of the present invention (i) uses an electrochemical measurement electrode chip which includes a working electrode on which a reactive substance which specifically reacts with a detection substance is at least partially fixed and (ii) includes the steps of: feeding the sample solution containing the detection substance into the measurement section via the inlet section; and measuring, under the presence of the chloride ion, the electrochemical active substance generated in a reaction of the reactive substance and the detection substance.

The configuration makes it possible to carry out accurate electrochemical measurement and analysis while preventing a peak from occurring due to a silver chloride complex ion.

In the electrochemical measurement electrode of the present invention, it is preferable that the working electrode, the reference electrode, and the silver ion capturing material are provided on an insulating substrate.

According to the configuration, the working electrode, the reference electrode, and the silver ion capturing material is provided on a single insulating substrate. This makes it possible to reduce an amount of the sample solution used in an electrochemical measurement.

In the electrochemical measurement electrode of the present invention, it is preferable that the silver ion capturing material includes a cation-exchange agent.

The term "cation-exchange agent" indicates a material which (i) captures a silver ion out of a silver chloride complex ion, (ii) exchange the silver ion for another cation (such as a sodium ion or a potassium ion), and (iii) discharge the another cation into the sample solution.

According to the configuration, the cation-exchange agent captures the silver ion in the silver chloride complex ion and discharges instead another cation which does not relate to the measurement. In this way, the silver chloride complex ion can be eliminated.

It is possible that the cation-exchange agent is made of one or both a cation-exchange resin and zeolite.

In the electrochemical measurement electrode of the present invention, it is preferable that the silver ion capturing material is made of a hardened material of a light-curing resin or a thermosetting resin, the light-curing resin or the thermosetting resin being mixed with the cation-exchange agent.

According to the configuration, the silver ion capturing material can be easily formed by light irradiation or heating.

In the electrochemical measurement electrode of the present invention, it is preferable that the silver ion capturing material contains a cation adsorbent.

The term "cation adsorbent" indicates a material which takes in a cation by a chemical binding (hydrogen binding, ion binding, coordinate binding). According to the configuration, the cation adsorbent takes in the silver ion in the silver chloride complex ion, and thereby the silver chloride complex ion can be eliminated.

It is possible that the cation adsorbent is made of (i) a chelate resin, ceramics, and mesoporous silica or (ii) any one of a chelate resin, ceramics, and mesoporous silica.

In the electrochemical measurement electrode of the present invention, it is preferable that the silver ion capturing material is made of a hardened material of a light-curing resin or a thermosetting resin, the light-curing resin or the thermosetting resin being mixed with the cation adsorbent.

According to the configuration, the silver ion capturing material can be easily formed by light irradiation or heating.

In the electrochemical measurement electrode of the present invention, it is preferable that the silver ion capturing material contains a silver ion reducing agent.

The term "silver ion reducing agent" indicate a material having a property of reducing a silver ion to silver. According to the configuration, the silver ion in the silver chloride complex ion is reduced to silver, and thereby the silver chloride complex ion can be eliminated.

It is possible that the silver ion reducing agent is a compound having an aldehyde group.

The compound having an aldehyde group is a compound which has a reductive capacity to reduce a silver ion to silver. Therefore, according to the configuration, the silver chloride complex ion can be eliminated.

It is possible that the silver ion reducing agent is made of a metal whose ionization tendency is higher than that of silver.

In a case where a solution, which contains two types of metal elements having respectively different ionization tendencies, is used, a metal element having a higher ionization tendency is ionized and becomes prone to emit an electron. On the other hand, a metal element having a lower ionization tendency receives the emitted electron and is thereby deposited as solid metal. With the use of this principle, the silver chloride complex ion can be eliminated. According to the configuration, the silver ion reducing agent is made of a metal having an ionization tendency higher than that of silver. Accordingly, the silver ion in the silver chloride complex ion receives an electron emitted in ionization of the metal, and thereby the silver ion is deposited as silver. This makes it possible to eliminate the silver chloride complex ion generated from the reference electrode.

It is preferable that the silver ion reducing agent is made of magnesium, aluminum, manganese, zinc, chromium, iron, cadmium, cobalt, tin, lead, or copper.

According to the configuration, it is possible to provide the electrochemical measurement electrode which can be used in a water system. In particular, in a case where the silver ion reducing agent is made of magnesium, aluminum, zinc, or copper, it is possible to provide the electrochemical measurement electrode which can be used in a water system and is safe in terms of toxicity and handiness.

In the electrochemical measurement electrode of the present invention, it is preferable that the silver ion capturing material is made of a hardened material of a light-curing resin or a thermosetting resin, the light-curing resin or the thermosetting resin being mixed with the silver ion reducing agent.

In the electrochemical measurement electrode of the present invention, it is preferable that the silver ion capturing material is made of a hardened material of a light-curing resin or a thermosetting resin, the light-curing resin or the thermosetting resin having a side chain to which an aldehyde group as a functional group is introduced.

According to the configuration, the silver ion capturing material can be easily formed by light irradiation or heating.

In the electrochemical measurement electrode of the present invention, it is preferable that the silver ion capturing material is disposed between the working electrode and the reference electrode.

The silver chloride complex ion generated from the reference electrode (i) is emitted in the sample solution, (ii) reaches the working electrode by dispersion, and (iii) is to be detected. According to the configuration, the silver ion capturing material is disposed between the working electrode and the reference electrode. This allows the silver ion capturing material to eliminate the silver chloride complex ion generated from the reference electrode before the silver chloride complex ion reaches the working electrode.

In the electrochemical measurement electrode of the present invention, it is preferable that the silver ion capturing material is disposed closer to the reference electrode than to the working electrode. Further, it is preferable that the silver ion capturing material is disposed in an area corresponding to a layer (i) which is formed around the reference electrode and (ii) in which a concentration gradient of the silver chloride complex ion is generated.

As described above, the silver chloride complex ion is generated from the reference electrode. According to the configuration, the silver ion capturing material is disposed closer to the reference electrode than to the working electrode. This allows the silver ion capturing material to eliminate the silver chloride complex ion so that the silver chloride complex ion is not emitted into the sample solution. In particular, the silver chloride complex ion can be eliminated more effectively in a case where the silver ion capturing material is disposed in the area corresponding to the layer (i) which is formed around the reference electrode and (ii) in which the concentration gradient of the silver chloride complex ion is generated.

In the electrochemical measurement electrode of the present invention, it is preferable that the silver ion capturing material is disposed closer to the working electrode than to the reference electrode. Further, it is preferable that the silver ion capturing material is disposed in an area corresponding to a diffusion layer which is formed around the working electrode.

According to the electrochemical measurement electrode, the silver chloride complex ion generated from the reference electrode flows in the sample solution and is detected by causing an electrochemical reaction at the working electrode. According to the configuration, the silver ion capturing material is disposed closer to the working electrode than to the reference electrode. This allows the silver ion capturing material to eliminate the silver chloride complex ion which has come closer to the working electrode. Accordingly, it is possible to prevent the silver chloride complex ion from causing an electrochemical reaction at the working electrode. In particular, in a case where the silver ion capturing material is disposed in the area corresponding to the diffusion layer formed around the working electrode, it is possible to eliminate the silver chloride complex ion more effectively.

In the electrochemical measurement electrode of the present invention, it is preferable that the silver ion capturing material is provided so as to at least partially cover the reference electrode.

According to the configuration, almost all the silver chloride complex ions generated from the reference electrode can be eliminated by the silver ion capturing material. This makes it possible to prevent the silver chloride complex ion from being emitted in the measuring system.

In the electrochemical measurement electrode of the present invention, it is preferable that the silver ion capturing material is provided so as to at least partially cover the working electrode.

According to the configuration, the silver ion capturing material eliminates almost all the silver chloride complex ions, which have been generated from the reference electrode and emitted into the sample solution, before the silver chloride complex ions reach the working electrode. This makes it possible to prevent the silver chloride complex ion from causing an electrochemical reaction at the working electrode.

In the electrochemical measurement electrode chip of the present invention, it is preferable that the silver ion capturing material is provided in at least part of the measurement section.

According to the configuration, it is possible to eliminate the silver chloride complex ion existing in the sample solution by the silver ion capturing material which is provided in at least part of the measurement section. This makes it possible to achieve reduction of an amount of the sample solution, reduction of measurement time, and simplification of analysis operation. Accordingly, an accurate and efficient measurement can be carried out.

In the electrochemical measurement electrode of the present invention, it is preferable that a reactive substance which specifically reacts with a detection substance is fixed on at least part of the working electrode.

According to the configuration, the reactive substance fixed on the working electrode specifically reacts with the detection substance. The detection substance can be detected by measuring an electrochemical active substance generated in the reaction. That is, with the use of the configuration, it is possible to provide a sensor.

In the electrochemical measurement electrode chip of the present invention, it is preferable that a reactive substance which specifically reacts with a detection substance is fixed on at least part of the working electrode.

According to the configuration, the reactive substance fixed on the working electrode specifically reacts with the detection substance. The detection substance can be detected by measuring an electrochemical active substance generated in the reaction. This makes it possible to (i) reduce an amount of a detection substance, (ii) reduce measurement time, and (iii) simplify analysis operation. That is, according to the configuration, it is possible to provide a sensor with which an analysis can be carried out in a short period of time.

In the electrochemical measuring method of the present invention using the above described electrochemical measurement electrode, it is preferable that the electrochemical active substance (i) contains para-aminophenol, potassium ferrocyanide, ferrocene, and a ferrocene derivative or (ii) is para-aminophenol, potassium ferrocyanide, ferrocene, or a ferrocene derivative. Moreover, in the electrochemical measuring method of the present invention using the above described electrochemical measurement electrode chip, it is preferable that the electrochemical active substance (i) contains para-aminophenol, potassium ferrocyanide, ferrocene, and a ferrocene derivative or (ii) is para-aminophenol, potassium ferrocyanide, ferrocene, or a ferrocene derivative.

According to the configuration, it is possible to carry out an accurate electrochemical measurement of the substance with which a redox reaction is detected with an electric potential of 1 V or less.

The present invention is not limited to the embodiments, but can be altered by a skilled person in the art within the scope of the claims. An embodiment derived from a proper combination of technical means disclosed in respective different embodiments is also encompassed in the technical scope of the present invention.

EXAMPLES

Example 1

Figure 34:
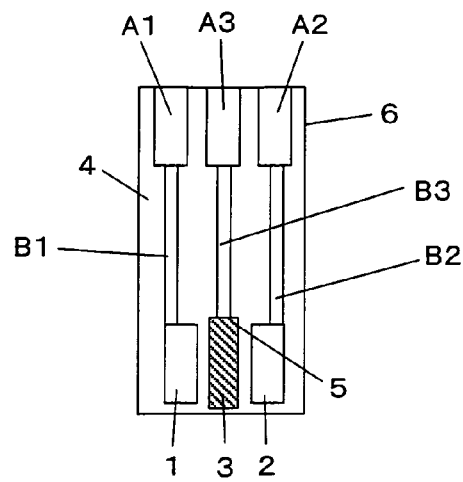
FIG. 34 is a top view illustrating a structure of the electrochemical measurement electrode produced in Example 1 or 2.
Figure 35:
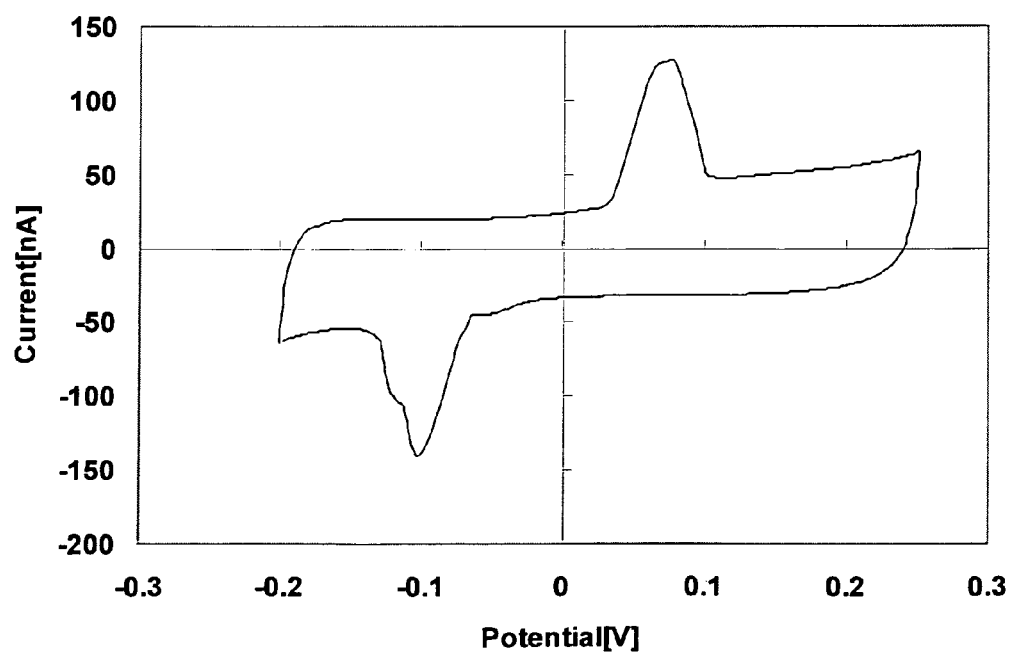
FIG. 35 is a graph illustrating abnormal peaks which appear when a CV measurement is carried out with the use of the electrochemical measurement electrode including a reference electrode, a working electrode, and a counter electrode.

FIG. 34 illustrates a configuration of an electrochemical measurement electrode prepared in Example 1. First, a working electrode 1 and a counter electrode 2 were provided on one edge part of an insulating substrate 6 (with thickness of 1 mm) made of glass of 1 cm×2 cm. Each of the working electrode 1 and the counter electrode 2 was a gold electrode having a size of 2 mm×5 mm. Then, a silver electrode having a size of 1 mm×5 mm was provided between the working electrode 1 and the counter electrode 2. A part of the silver electrode was chemically changed to silver chloride so as to provide a reference electrode 3 made of silver and silver chloride on the insulating substrate 6.

Further, connection pads A1 through A3 each having a size of 2 mm×5 mm were provided on the other edge part of the insulating substrate 6. Then, leading electrode sections B1 through B3 were provided so as to connect the connection pads A1 through A3 with the working electrode 1, the counter electrode 2, and the reference electrode 3, respectively. The connection pads A1 through A3 and the leading electrode sections B1 through B3 were all made by gold. Note that the working electrode 1, the counter electrode 2, the reference electrode 3, the connection pads A1 through A3, and the leading electrode sections B1 through B3 were provided on the insulating substrate 6 by sputtering.

A cation-exchange resin was mixed with a water-soluble photosensitive resin (BIOSURFINE (registered trademark)-AWP, manufactured by Toyo Gosei Co., Ltd.), and the mixture was dripped so as to cover the reference electrode 3. Thus dripped mixture was hardened by exposing the mixture to light so as to form a silver ion capturing material 4 covering the reference electrode 3.

Figure 36:
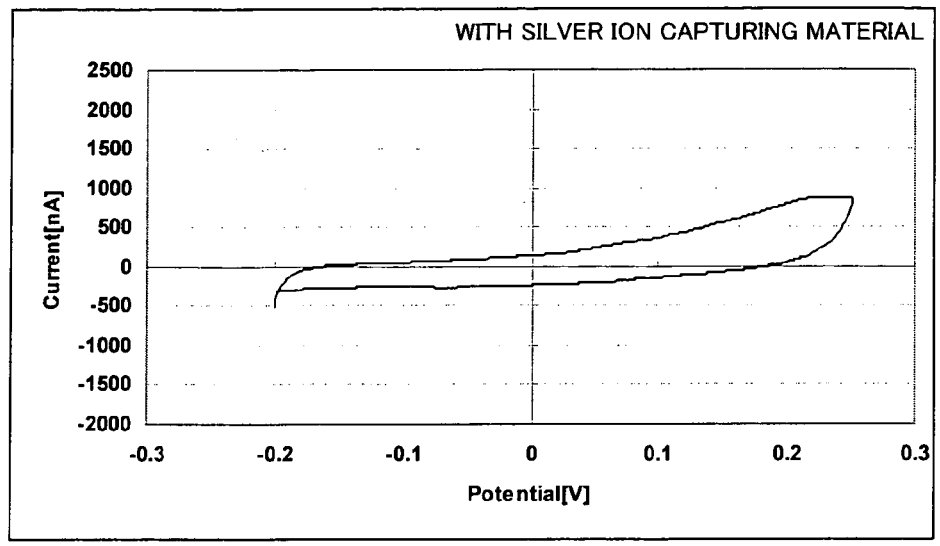
FIG. 36 is a graph illustrating a CV curve of tris-buffer measured with the use of the electrochemical measurement electrode including the silver ion capturing material, in Example.

A CV measurement of a tris-buffer was carried out with the use of thus prepared electrochemical measurement electrode. FIG. 36 is a graph illustrating a CV curve showing a result of the CV measurement.

Comparative Example 1

Figure 37:
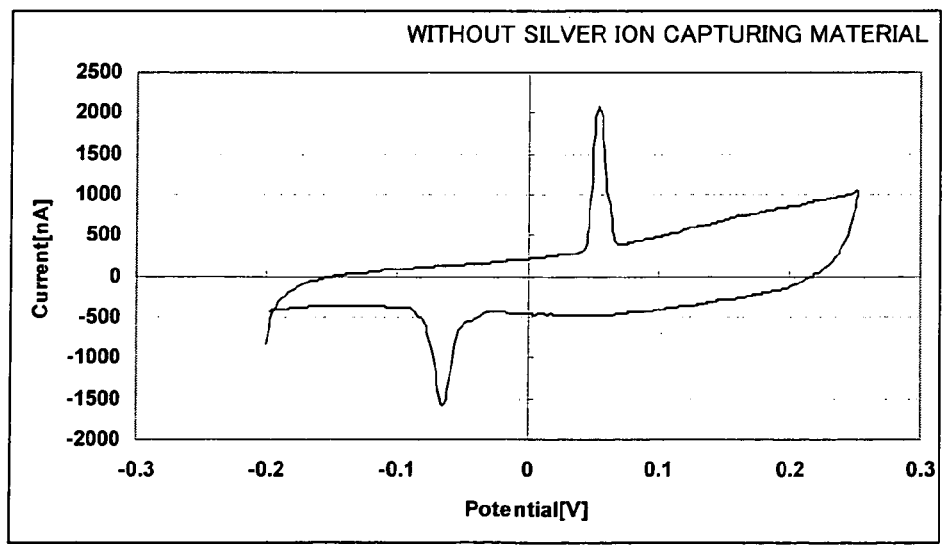
FIG. 37 is a graph illustrating a CV curve measured with the use of an electrochemical measurement electrode which does not include a silver ion capturing material.

An electrochemical measurement electrode including no silver ion capturing material 4 was prepared as Comparative Example 1. Then, a CV measurement of a tris-buffer was carried out with the use of the electrochemical measurement electrode, as with Example 1. FIG. 37 is a graph illustrating a CV curve showing a result of the CV measurement.

The CV measurement was carried out with the use of the electrochemical measurement electrode including no silver ion capturing material 4, and peaks were detected around ±50 mV as shown in FIG. 37. The peaks were abnormal peaks occurred due to the silver chloride complex ion. On the other hand, when the CV measurement was carried out with the use of the electrochemical measurement electrode including the silver ion capturing material 4, such a peak was not detected.

Figure 38:
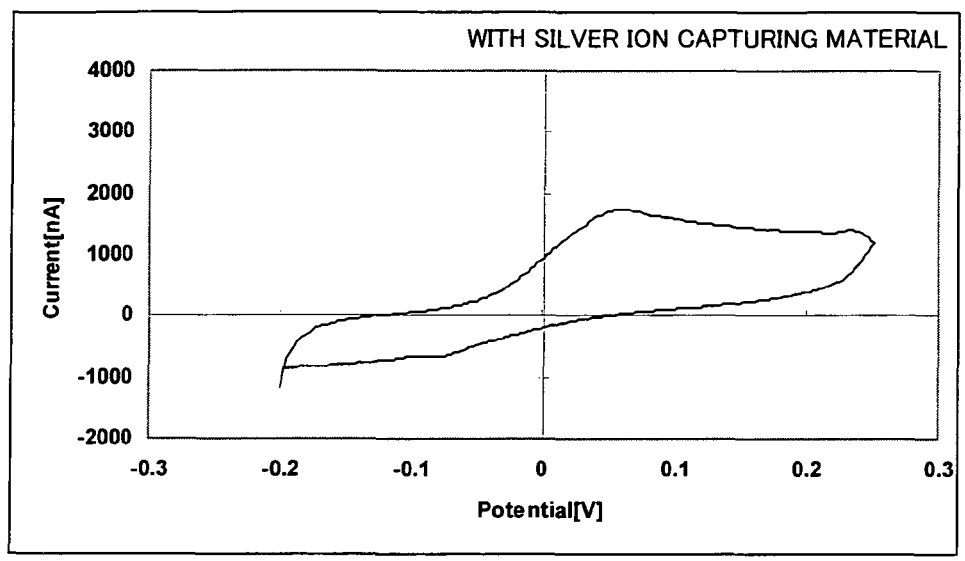
FIG. 38 is a graph illustrating a CV curve of a para-aminophenol (pAP) measured with the use of the electrochemical measurement electrode of Example 1.
Figure 39:
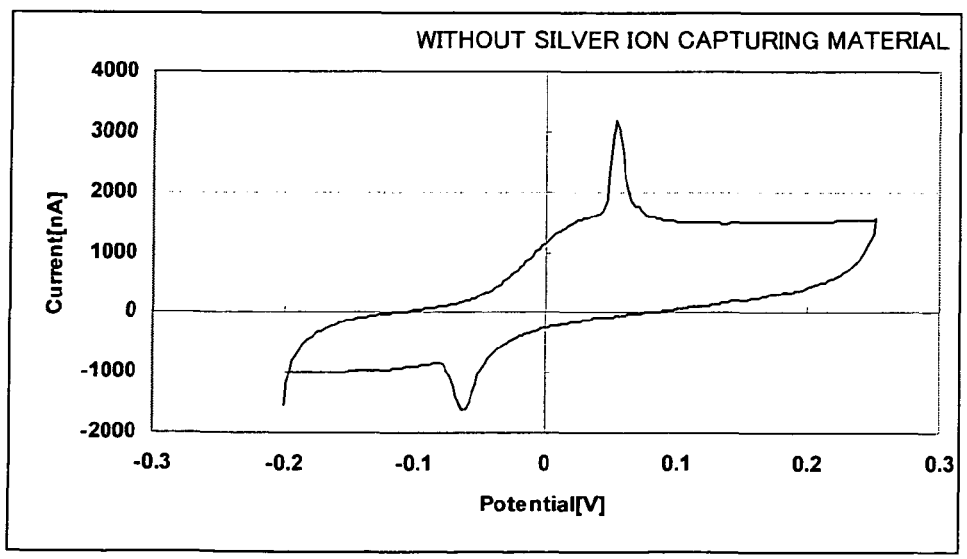
FIG. 39 is a graph illustrating a CV curve of a para-aminophenol (pAP) measured with the use of an electrochemical measurement electrode of Comparative Example 1.

Further, a CV measurement of a sample solution containing 50 μM of para-aminophenol (pAP) as an electrochemical active substance was carried out with the use of the electrochemical measurement electrodes of Example 1 and Comparative Example 1. FIG. 38 is a graph illustrating a CV curve of a para-aminophenol (pAP) measured with the use of the electrochemical measurement electrode of Example 1. FIG. 39 is a graph illustrating a CV curve of a para-aminophenol (pAP) measured with the use of an electrochemical measurement electrode of Comparative Example 1.

As shown in FIG. 39, in the case where the electrochemical measurement electrode including no silver ion capturing material 4 (Comparative Example 1) was used, peaks of pAP overlapped with the peaks around ±50 mV (the abnormal peaks occurred due to the silver chloride complex ion) and thereby an accurate current could not be read out. On the other hand, in the case where the electrochemical measurement electrode including the silver ion capturing material 4 (Example 1) was used, no abnormal peak occurred due to the silver chloride complex ion, and a peak of only pAP was detected (see FIG. 38). Accordingly, a current could be read out accurately.

Example 2

An electrochemical measurement electrode was prepared in a similar way to Example 1, except that a material of the silver ion capturing material 4 is different from that of the electrochemical measurement electrode shown in FIG. 34.

As with Example 1, a chelate resin (DIAION CR20, manufactured by Mitsubishi Chemical Corporation) was mixed with a water-soluble photosensitive resin (BIOSURFINE (registered trademark)—AWP, manufactured by Toyo Gosei Co., Ltd.), and the mixture was dripped so as to cover the reference electrode 3. The dripped mixture was hardened by exposing the mixture to light so as to form a silver ion capturing material 4 covering the reference electrode 3.

The chelate resin used in this Example is a resin which does not generate a chelate with (i) an alkali metal such as a potassium ion or a sodium ion and (ii) an alkali earth metal such as a magnesium ion or a calcium ion, whereas selectively captures a metal ion such as a silver ion.

A CV measurement of a phosphate buffer and a CV measurement of pAP were carried out with the use of the electrochemical measurement electrodes of Example 2 and Comparative Example 1. Then, the measurement results regarding the electrochemical measurement electrodes of Example 2 and Comparative Example 1 were compared with each other.

As a result, as with the result of comparison between Example 1 and Comparative Example 1, in the case where the CV measurement of the phosphate buffer was carried out with the use of the electrochemical measurement electrode including no silver ion capturing material 4 (Comparative Example 1), peaks were detected around ±50 mV. On the other hand, in the case where the CV measurement of the phosphate buffer was carried out with the use of the electrochemical measurement electrode including the silver ion capturing material 4 (Example 2), such a peak was not detected.

Further, in the case where the CV measurement of pAP was carried out with the use of the electrochemical measurement electrode including no silver ion capturing material 4 (Comparative Example 1), peaks of pAP overlapped with the peaks around ±50 mV and thereby an accurate current could not be read out. On the other hand, in the case where the electrochemical measurement electrode including the silver ion capturing material 4 (Example 2) was used, a peak of only pAP was detected. Accordingly, a current could be read out accurately.

INDUSTRIAL APPLICABILITY

As described above, the present invention can provide an electrochemical measurement electrode with which an accurate electrochemical measurement can be carried out. Therefore, industrial applicability of the present invention is high.

REFERENCE SIGNS LIST

1: Working electrode
2: Counter electrode
3: Reference electrode
A1 through A3: Electrode pad
B1 through B3: Leading electrode section
4: Silver ion capturing material
5: Electrode holder
6: Insulating substrate
7: Measurement section
8: Inlet section
9: Outlet section
10: Chip substrate

The invention claimed is:

1. An electrochemical measuring method comprising: an electrochemical measurement electrode chip comprising (I) an electrochemical measurement electrode configured to carry out a CV (cyclic voltammetry) measurement of an electrochemical active substance in a sample solution containing a chloride ion, the electrochemical measurement electrode including (i) a working electrode, (ii) a counter electrode, (iii) a reference electrode made of silver and silver chloride, and (iv) a silver ion capturing material which captures a silver ion out of a silver chloride complex ion generated from the reference electrode, wherein the silver ion capturing material contains a cation-absorbent, and (II) a microchip which covers the electrochemical measurement electrode, the microchip having (i) a hollowed section which contains therein the working electrode and the reference electrode and (ii) an inlet section via which the sample solution is fed to the measurement section which is an area defined by the electrochemical measurement electrode and the hollowed section, the silver ion capturing material existing in the area defined by the electrochemical measurement electrode and the hollowed section, said electrochemical measuring method comprising the steps of:

feeding the sample solution containing the chloride ion and the electrochemical active substance into the measurement section via the inlet section; and measuring the electrochemical active substance in the sample solution.

2. The electrochemical measuring method as set forth in claim 1, wherein:

the electrochemical active substance (i) contains para-aminophenol, potassium ferrocyanide, ferrocene, and a ferrocene derivative or (ii) is a para-aminophenol, potassium ferrocyanide, ferrocene, or ferrocene derivative.

3. An electrochemical measuring method comprising: an electrochemical measurement electrode configured to carry out a CV (cyclic voltammetry) measurement of an electrochemical active substance in a sample solution containing a chloride ion, the electrochemical measurement electrode comprising (i) a working electrode, (ii) a counter electrode, (iii) a reference electrode made of silver and silver chloride, and (iv) a silver ion capturing material which captures a silver ion out of a silver chloride complex ion generated from the reference electrode, wherein the silver ion capturing material contains a cation-absorbent, and wherein a reactive substance which specifically reacts with a detection substance is fixed on at least part of the working electrode, said electrochemical measuring method comprising the steps of:

dipping the electrochemical measurement electrode in the sample solution containing the chloride ion and the electrochemical active substance, the electrochemical measurement electrode being dipped so that, at least partially, each of the working electrode, the reference electrode and the silver ion capturing material contacts with the sample solution; and measuring the electrochemical active substance in the sample solution.

4. The electrochemical measuring method as set forth in claim 3, wherein:

the electrochemical active substance (i) contains para-aminophenol, potassium ferrocyanide, ferrocene, and a ferrocene derivative or (ii) is a para-aminophenol, potassium ferrocyanide, ferrocene, or ferrocene derivative.

5. An electrochemical measurement electrode chip, comprising:

an electrochemical measurement electrode configured to carry out a CV (cyclic voltammetry) measurement of an electrochemical active substance in a sample solution containing a chloride ion, the electrochemical measurement electrode comprising (i) a working electrode, (ii) a counter electrode (iii) a reference electrode made of silver and silver chloride, and (iv) a silver ion capturing material which captures a silver ion out of a silver chloride complex ion generated from the reference electrode, wherein the silver ion capturing material contains a cation-absorbent; and a microchip which covers the electrochemical measurement electrode, the microchip having (i) a hollowed section which contains therein the working electrode and the reference electrode and (ii) an inlet section via which the sample solution is fed into a measurement section which is an area defined by the electrochemical measurement electrode and the hollowed section, the silver ion capturing material existing in the area defined by the electrochemical measurement electrode and the hollowed section.

6. The electrochemical measurement electrode chip as set for the in claim 5, wherein:

the silver ion capturing material is provided in at least part of the measurement section.

7. The electrochemical measurement electrode chip as set forth in claim 5, wherein:

a reactive substance which specifically reacts with a detection substance is fixed on at least part of the working electrode.

8. An electrochemical measurement electrode configured to carry out a CV (cyclic voltammetry) measurement of an electrochemical active substance in a sample solution containing a chloride ion, said electrochemical measurement electrode comprising:

a working electrode;
counter electrode;
a reference electrode made of silver and silver chloride; and
a silver ion capturing material which captures a silver ion out of a silver chloride complex ion generated from the reference electrode, wherein the silver ion capturing material contains a cation-absorbent, and wherein a reactive substance which specifically reacts with a detection substance is fixed on at least part of the working electrode.

9. The electrochemical measurement electrode as set forth in claim 8, wherein:

the working electrode, the reference electrode and the silver ion capturing material are provided so as to contact with the sample solution.

10. The electrochemical measurement electrode as set forth in claim 8, wherein:

the working electrode, the reference electrode, and the silver ion capturing material are provide on an insulating substrate.

11. The electrochemical measurement electrode as set forth in claim 8, wherein:

the cation absorbent is made of (i) a chelate resin, ceramics, and mesoporous silica or (ii) any one of a chelate resin, ceramics, and mesoporous silica.

12. The electrochemical measurement electrode as set forth in claim 8, wherein:

the silver ion capturing material is made of a hardened material of a light-curing resin or a thermosetting resin, the light-curing resin or the thermosetting resin being mixed with the cation absorbent.

13. The electrochemical measurement electrode as set forth in claim 8, wherein:

the silver ion capturing material is disposed between the working electrode and the reference electrode.

14. The electrochemical measurement electrode as set forth in claim 8, wherein:

the silver capturing material is disposed closer to the reference electrode than to the working electrode.

15. The electrochemical measurement electrode as set forth in claim 14, wherein:

the silver ion capturing material is displayed in an area corresponding to a layer (i) which is formed around the reference electrode and (ii) in which a concentration gradient of the silver chloride complex ion is generated.

16. The electrochemical measurement electrode as set forth in claim 8, wherein:

the silver ion capturing material is disposed closer to the working electrode than to the reference electrode.

17. The electrochemical measurement electrode as set forth in claim 16, wherein:

the silver ion capturing material is disposed in an area corresponding to a diffusion layer which is formed around the working electrode.

18. The electrochemical measurement electrode as set forth in claim 8, wherein:

the silver ion capturing material is provided so as to at least partially cover the reference electrode.

19. The electrochemical measurement electrode as set forth in claim 8, wherein:

the silver ion capturing material is provided so as to at least partially cover the working electrode.

* * * * *